United States Patent [19]

Sloan

[11] 4,381,307
[45] Apr. 26, 1983

[54] SOFT TERTIARY AMINE ESTERS OF BIO-AFFECTING CARBOXYLIC ACIDS

[75] Inventor: Kenneth B. Sloan, Gainesville, Fla.

[73] Assignee: Merck & Co., Inc., Rahway, N.J.

[21] Appl. No.: 202,750

[22] Filed: Oct. 31, 1980

[51] Int. Cl.³ .................... A61K 31/43; A61K 31/56; C07J 7/00
[52] U.S. Cl. .................. 424/271; 260/239.5; 260/239.1; 260/397.45; 260/397.1; 560/121; 560/146; 424/238; 424/239; 424/313; 424/243
[58] Field of Search ............ 260/397.1, 397.45, 239.1; 424/238, 239, 271, 313, 241, 243; 560/146

[56] References Cited

U.S. PATENT DOCUMENTS 4,218,451 8/1980 Feyen et al. .................. 424/271
4,241,062 12/1980 Hannah .................. 424/271
4,260,625 4/1981 Hardy et al. .................. 424/271

*Primary Examiner*—Elbert L. Roberts
*Attorney, Agent, or Firm*—Theresa Y. Cheng; Michael C. Sudol, Jr.; Mario A. Monaco

[57] ABSTRACT

Novel derivatives of known bio-affecting carboxylic acids R-COOH are disclosed, said derivatives having the structural formula

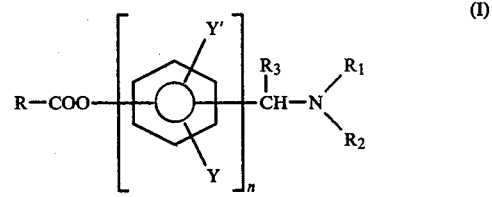

(I)

wherein Y and Y' are each H or $C_1$–$C_4$ alkyl; n is 0 or 1; $R_1$ and $R_2$ are each selected from a variety of unsubstituted or substituted hydrocarbon radicals, or are combined so that —$NR_1R_2$ represents the residue of a saturated or unsaturated heterocyclic compound containing one secondary nitrogen atom; and $R_3$ is H or one of a variety of other substituents. Salts and N-oxides of compounds of formula (I) and the corresponding diacyloxy derivatives of known bio-affecting carboxylic acids HOOC-R'-COOH are disclosed also. The parent acids from which the subject soft tertiary amine esters can be derived include such bio-affecting agents as cephalosporin and penicillin antibiotics, amino acids and structurally related compounds, prostaglandins and their metabolites, steroidal anti-inflammatory agents, and non-steroidal anti-inflammatory/non-narcotic analgesic/antipyretic agents.

31 Claims, No Drawings

SOFT TERTIARY AMINE ESTERS OF BIO-AFFECTING CARBOXYLIC ACIDS

TECHNICAL FIELD OF THE INVENTION

The present invention relates to novel and useful biologically active derivatives of bio-affecting carboxylic acids. In particular, the present invention relates to novel soft tertiary amine ester derivatives of bioaffecting compounds containing one or two carboxylic acid functions.

BACKGROUND OF THE PRIOR ART:

It is well-known that a wide variety of compounds containing carboxylic acid functions are biologically active. For example, such structure is characteristic of non-steroidal anti-inflammatory/non-narcotic analgesic agents such as indomethacin, aspirin, naproxen and the like; cephalosporin antibiotics, e.g. cefmetazole, cefazolin, cephalexin, etc.; penicillin antibiotics such as ampicillin, amoxicillin, hetacillin and the like; as well as other compounds having diverse properties and structures (e.g. captopril, an anti-hypertensive; carbidopa, a peripheral decarboxylase inhibitor; chlorambucil, an antineoplastic; protaglandins $E_1$, $E_2$ and $F_{2\alpha}$; and numerous others).

Nevertheless, it is also well-known that such prior art compounds are characterized by certain inherent disadvantages, notably serious bioavailability and physiological availability problems upon administration. Such reduced availability is attributed in part to significant ionization of the carboxylic acid functional group at physiological pH, which results in the fact that such compounds are poorly absorbed through lipid-water membrane barriers and are irritating.

Thus, a clear need exists for new derivatives of the known bio-affecting acids which will be devoid of the disadvantages inherent in those prior art compounds.

A few compounds structurally related to certain compounds of formula (I) have been reported in the literature. Thus, Böhme and Backhaus, in *Liebigs Ann. Chem.* 1975, 1790-1796 and *Liebigs Ann. Chem.* 1975, 1952-1955, describe acyloxymethyl(dialkylamines) wherein the acyl group is

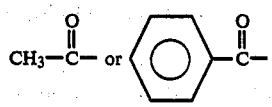

and wherein the alkyl groups are each methyl. Volz and Ruchti, in *Liebigs Ann. Chem.* 1977, 33-39 describe compounds of the type

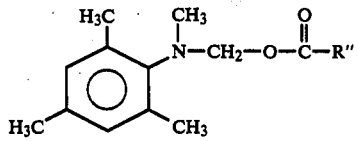

wherein R" is D, H$_3$, CD$_3$, C$_6$H$_5$, C$_6$H$_5$-Cl(m), CH$_2$OCH$_3$, CH$_2$Cl and CHCl$_2$. Also, in "Iminium Salts in Organic Chemistry", ed. H. Böhme and H. G. Viehe, From *Advances in Organic Chemistry*, ed. E. C. Taylor, Volume 9, Part 1, John Wiley & Sons, Inc., acyloxymethyl(dimethylamines) where the acyl group is acetyl, chloroacetyl, trichloroacetyl and trifluoroacetyl are described, as are the compounds

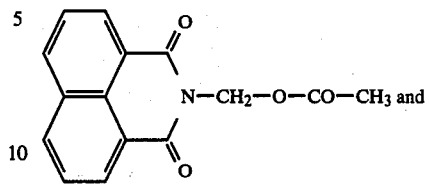

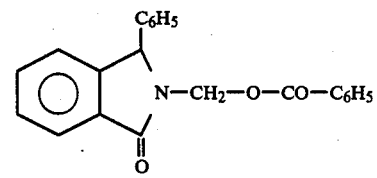

However, none of the publications disclose any utility for the compounds described therein. There is no disclosure or hint of any kind in the literature that such compounds would have pharmaceutical or other bio-affecting utility, or that they would be highly advantageous delivery systems for their parent acids. Also, many of the prior art compounds, e.g. the dimethylamines, are very unstable and difficult to purify, thus would be unsatisfactory for purposes of the present invention. Yet, apparently no systematic investigation was made to find a way to stabilize those compounds.

SUMMARY OF THE INVENTION

It is one object of the present invention to provide novel derivatives of conventional bio-affecting carboxylic acids which elicit the bio-affecting (e.g. pharmacological) response characteristic of the acids from which they are derived when administered to warm-blooded animals, yet which are characterized as having good biphasic solubility and thus being less irritating and more permeable through biological membranes, e.g. skin, gut, buccal or rectal mucosa, than are the parent compounds.

It is another object of the present invention to provide such derivatives of conventional bio-affecting carboxylic acids which are capable of providing a higher level of bioavailability than that possible with the parent compounds.

It is another object of the present invention to provide such derivatives of conventional bio-affecting carboxylic acids which are highly stable under acidic conditions (e.g. before and during absorption into the body), yet are easily cleaved in vivo as they reach systemic circulation and more basic conditions (i.e. higher pH levels) to achieve the desired biological effect.

It is yet another object of the present invention to provide such derivatives of conventional bio-affecting carboxylic acids which are "soft" in nature, i.e. which are characterized by in vivo destruction to essentially nontoxic moieties, after they have achieved their desired therapeutic (or other desired bio-affecting) role.

Other objects, features and advantages of the invention will be apparent to those skilled in the art from the detailed description of the invention which follows.

The foregoing objects, features and advantages are provided by the novel compounds of the formula

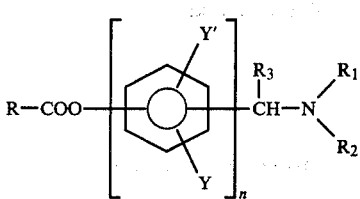

(I)

wherein R—COO— is the acyloxy residue of a bio-affecting monocarboxylic acid, with the proviso that R—COO— cannot be the acyloxy residue of formic acid, acetic acid, chloroacetic acid, methoxyacetic acid, dichloroacetic acid, trichloroacetic acid, trifluoroacetic acid, benzoic acid or chlorobenzoic acid; Y and Y', which can be the same or different, are each hydrogen or alkykl of 1 to 4 carbon atoms; n is zero or one; the depicted phenylene group is oriented such that R—COO— and —CH($R_3$)$NR_1R_2$ are positioned ortho or para to each other; $R_1$ and $R_2$, which can be the same or different, are each alkyl of 1 to 10 carbon atoms; alkenyl of 2 to 10 carbon atoms; aryl of 6 to 10 carbon atoms; cycloalkyl of 3 to 8 carbon atoms; cycloalkenyl of 4 to 8 carbon atoms; alkynyl of 2 to 10 carbon atoms; aralkyl, alkaryl, aralkenyl, aralkynyl, alkenylaryl, or alkynylaryl, wherein the alkyl, alkenyl, alkynyl, and aryl protions are defined as above; or a substituted derivative of one of the above-defined alkyl, alkenyl, aryl, cycloalkyl, cycloalkenyl, alkynyl, aralkyl, alkaryl, aralkenyl, aralkynyl, alkenylaryl and alkynylaryl radicals, said derivative having one or more substituents each of which are selected from the group consisting of $C_1$-$C_8$ alkyl, $C_1$-$C_8$ alkoxy, $C_1$-$C_8$ alkanoyl, $C_1$-$C_8$ alkanoyloxy, halo, cyano, $C_2$-$C_9$ carbalkoxy, $C_1$-$C_8$ alkylthio, nitro, $C_1$-$C_8$ haloalkyl having 1 or more halo substituents, dialkylamino wherein the alkyl portions each contain 1 to 8 carbon atoms, carboxy, dialkylcarbamyl wherein the alkyl portions each contain 1 to 8 carbon atoms, and $C_1$-$C_8$ alkylsulfonyl; or $R_1$ or $R_2$ are combined so that —$NR_1R_2$ represents the residue of a saturated or unsaturated heterocyclic compound containing one secondary nitrogen atom; and $R_3$ is hydrogen, $R_1'$,

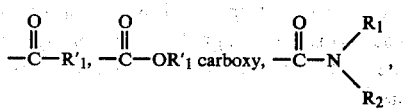

—$CH_2OCOR_1'$, —$CH_2ONO_2$, $CX_3$, 2-pyridyl, 3-pyridyl, 4-pyridyl, 2-furyl, cyano, carbamyl or $C_2$-$C_9$ alkylcarbamyl, wherein $R_1$ and $R_2$ are as defined above, X is Cl or Br, and $R_1'$ is any radical encompassed by the definition of $R_1$ above; the novel compounds of the formula

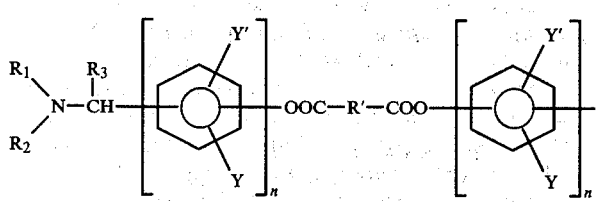 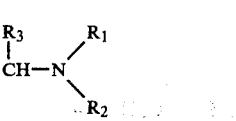

(II)

wherein —OOC—R'—COO— is the di(acyloxy) residue of a bio-affecting dicarboxylic acid; the groups attached to each end of the divalent —OOC—R'—COO— residue are identical to each other; and Y, Y', n, $R_1$, $R_2$, —$NR_1R_2$, $R_3$ and the orientation of the depicted phenylene groups are as defined with respect to formula (I) above; and the non-toxic pharmaceutically acceptable acid addition salts and N-oxides of the compounds of formulas (I) and (II).

DETAILED DESCRIPTION OF THE INVENTION

The term "nontoxic pharmaceutically acceptable acid addition salt" as used herein generally includes the nontoxic acid addition salts of selected compounds of formulas (I) and (II), formed by reaction of those compounds with nontoxic inorganic or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, methanesulfonic, toluensulfonic, and the like. These salts can be formed via typical methodology.

The term "N-oxide" as used herein includes the nontoxic pharmaceutically acceptable N-oxides of selected compounds of formulas (I) and (II). The N-oxides are prepared by oxidation of the selected compounds of formulas (I) and (II) with a suitable oxidizing agent, e.g. m-chloroperbenzoic acid or hydrogen peroxide, in an appropriate inert solvent such as dichloromethane, benzene or chloroform, at a temperature of from 0° C. to room temperature, for 1 to 8 hours, followed by isolation in the usual manner.

The term "acyloxy residue" as used herein with respect to any bio-affecting monocarboxylic acid is intended to represent that part of the bio-affecting parent compound which remains after removal of the hydrogen atom from the —COOH portion of the molecule. Similarly, the term "di(acyloxy) residue" as used herein with respect to any bio-affecting dicarboxylic acid is intended to represent that part of the bio-affecting parent compound which remains after removal of the hydrogen atom from each of the —COOH portions of the molecule.

With respect to the radicals encompassed by $R_1$, $R_2$ and —$NR_1R_2$ in formulas (I) and (II) and throughout this specification, the following definitions are applicable:

The expression "the residue of a saturated or unsaturated heterocyclic compound containing one secondary nitrogen atom" as used herein is intended to indicate that portion of the heterocyclic compound H-$NR_1R_2$ which remains after removal of the hydrogen atom from the secondary nitrogen. Thus, the term "saturated or unsaturated heterocyclic compound containing one secondary nitrogen atom" encompasses saturated monocycles containing one or more hetero atoms in the ring, optionally bearing one or more substituents such as phenyl, benzyl and methyl; and unsaturated one and two ring systems containing one or more double bonds and one or more ring hetero atoms, optionally substituted with one or more methyl groups. In every case, the substituents and double bonds, if any, must be located such that the parent heterocyclic compound from which the residue —$NR_1R_2$ is derived is a compound of the formula $HNR_1R_2$, i.e., the parent compound invariably contains one N which is a secondary nitrogen atom. When the parent heterocycle contains more than one nitrogen atom, one nitrogen must be a secondary nitrogen and any other nitrogen must be tertiary. In any case, the parent compound can contain other hetero atoms, e.g. sulfur and/or oxygen. Illustrative of residues of saturated monocyclic heterocyclics which are encompassed by the —$NR_1R_2$ term are morpholino, perhydro-1,2,4-oxathiazin-4-yl, 1-pyrrolidinyl, 4-benzyl-1-piperazinyl, 4-methyl-1-piperazinyl, piperidino, hexamethyleneimino, 4-phenylpiperidino, 2-methyl-1-pyrazolidinyl, 3-methyl-1-imidazolidinyl, 4-benzylpiperidino and 4-phenyl-1-piperazinyl. Exemplary of residues of unsaturated one and two ring heterocyclic systems represented by —$NR_1R_2$ are radicals such as 1-imidazolyl, 1-pyrrolyl, 1-pyrazolyl, 1-indolinyl, 2-isoindolinyl, 1-indolyl, 2-isoindolyl, 1H-indazol-1-yl, and 7-purinyl; and radicals derived from compounds such as pyrazoline, pyrroline and imidazoline wherein there is one secondary nitrogen atom, e.g., radicals of the type

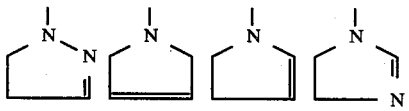

and the like. In addition, any of the aforesaid unsaturated one and two ring heterocycles can be optionally substituted with one or more methyl groups.

The term "aryl" as used herein can be exemplified by phenyl and naphthyl.

In addition, here and throughout this specification, the following examples are applicable: The alkyl radicals include methyl, ethyl, propyl and butyl and the branched-chain isomers thereof, as well as their straight and branched-chain higher homologues in the instances where "alkyl" can contain more than 4 carbon atoms. The alkenyl and alkynyl radicals may be straight or branched-chain, for example, vinyl, propenyl, butenyl, ethynyl, propynyl, butynyl, and the like. The cycloalkyl and cycloalkenyl radicals are exemplified by cyclopentyl, cyclohexyl and cyclopentenyl. The aralkyl, aralkenyl and aralkynyl radicals are of the type.

-alkylene-aryl
-alkenylene-aryl
and
-alkynylene-aryl wherein aryl is as defined above and the alkylene, alkenylene and alkynylene moieties contain up to 10 carbon atoms (preferably up to 6 carbon atoms) and can be straight or branched-chain. The alkylene moieties are typified by methylene, ethylene, propylene, trimethylene, 1,2-butylene, 2,3-butylene, tetramethylene and the like. Exemplary of the contemplated alkenylene and alkynylene moieties are vinylene, ethynylene, butenylene and butynylene. Additionally, the alkoxy, alkanoyl, alkanoyloxy, carbalkoxy, alkylthio, dialkylamino, dialkylcarbamyl, alkylsulfonyl and alkylcarbamyl radicals are of the type —O—alkyl

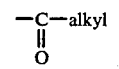

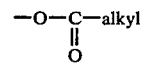

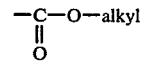

—S—alkyl

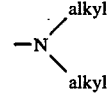

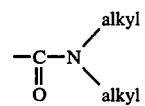

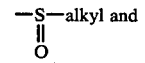

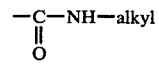

—C—NH—alkyl
‖
O respectively, wherein the alkyl group in each instance contains 1 to 8 carbon atoms.

The bio-affecting carboxylic acids from which the compounds of the present invention can be considered to be derived are legion. In essence, the present inventor has found that any compound which contains one or two carboxylic acid functional groups and which is biologically active can be advantageously derivatized according to the present invention to afford the corresponding compounds of formulas (I) and (II) and their pharmaceutically acceptable acid addition salts and N-oxides, which derivatives exhibit the advantages indicated hereinabove as to improved bioavailability, etc. as compared to their parent acids. However, the compounds of formulas (I) and (II) having low pKa's are preferred, e.g. the compounds derived from the less basic amines, e.g. imidazole, pyrazole, pyrrole and the like, because of their enhanced stability and greater bioavailability. Other preferred derivatives of the invention with relatively low pKa's (and consequent improved stability and bioavailability) can be prepared by first preparing a compound of formula (I) or (II) wherein the —$NR_1R_2$ portion is derived from a highly basic amine, e.g. dimethylamine, morpholine or the like, and then forming the N-oxide of the resultant compound of formula (I) or (II). Also, as will be clear from the discussion and examples which follow, in some cases the parent carboxylic acids contain reactive moieties (in addition to the carboxy group) which must be protected during the reaction which forms the soft tertiary amine esters. The protecting groups are then subsequently removed to afford the desired compounds of the invention.

One important group of bio-affecting carboxylic acids which can be derivatized according to the present invention consists of the non-steroidal anti-inflammatory/non-narcotic analgesic/anti-pyretic agents. Especially significant members of this group are indomethacin, aspirin, naproxen, fenoprofen, sulindac, ibuprofen, tolmetin, diflunisal, flurbiprofen, indoprofen, mefenamic acid, fenclozic acid, ketoprofen, alclofenac, bucloxic acid, meclofenamic acid, flufenamic acid, cinchophen, voltaren, cinmetacin, ibufenac, furobufen, fenclofenac, prodolic acid, pirprofen, oxoprozin, clonixin, fluprofen, flutiazin, salicylic acid, niflumic acid, clometacin, flufenisal, salsalate and flunixin. Other acids belonging to this group, i.e. non-steroidal acids having anti-inflammatory, analgesic and/or anti-pyretic properties, for example, o-(carbamoylphenoxy)acetic acid, salicilsalicylic acid and salicylsulfuric acid, will be apparent to those skilled in the art. Also some members of this group are known to be useful for other purposes, e.g. in the treatment of rheumatic fever and other kinds of arthritis, as keratolytics, etc.

Another significant group of bio-affecting carboxylic acids which can be derivatized to form the compounds of the present invention comprises the cephalosporin antibiotics. Generally speaking, members of this group of antibacterial agents have the skeletal structure

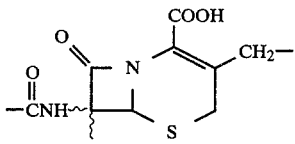

the free valences being satisfied by a variety of different substituents which do not adversely affect the antibiotic/antibacterial properties of the resultant compounds. Suitable substituents are known to those skilled in the art and also will be readily apparent from the known structures of the particular cephalosporins named below. Especially significant members of this group include cefmetazole, cefazolin and cephalexin. Examples of other parent carboxylic acids in this category include cefoxitin, cephacetrile, cephaloglycin, cephaloridine, cephalosporin C, cephalothin, cephamycin A, cephamycin B, cephamycin C, cephapirin and cephradine. Still other suitable parent acids will be apparent to those skilled in the art.

Yet another group of bio-affecting carboxylic acids which can be derivatized to form the compounds of the present invention comprises the penicillin antibiotics. Generally, members of this group of antibacterial or antimicrobial agents are characterized by the skeletal structure

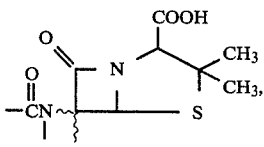

the free valences being satisfied by various substituents which do not adversely effect the antibiotic properties of the resultant compounds. Appropriate substituents are known to those skilled in the art and will also be apparent from the known structures of the particular penicillins named below. Particularly noteworthy members of this group of parent acids include ampicillin, amoxicillin and hetacillin. Other significant parent acids in this category include carfecillin, carindacillin, carbenicillin, amylpenicillin, azidocillin, benzylpenicillinic acid, clometacillin, cloxacillin, cyclacillin, methicillin, nafcillin, 2-pentenylpenicillin, penicillin BT, penicillin N, penicillin O, penicillin S, penicillin V (phenoxymethyl penicillin), chlorobutin penicillin, dicloxacillin, diphenicillin, heptylpenicillin and metampicillin. However, this listing is not intended to be exhaustive and other acids in this category will be apparent to those skilled in the art.

Another significant group of bio-affecting parent carboxylic acids comprises amino acids and structurally related compounds. Especially important members of this group include GABA (γ-aminobutyric acid), an anticonvulsant; captopril, an antihypertensive; carbidopa, a peripheral decarboxylase inhibitor, used in combination with levodopa in the treatment of parkinsonism; methyldopa, an antihypertensive; thyroxine, the l-form being used as thyroid hormone and the D-form as anticholesteremic; and levodopa, an anticholinergic and antiparkinsonian agent. Yet other members of this group include the naturally occurring amino acids (glycine, alanine, valine, leucine, isoleucine, phenylalanine, proline, tryptophan, serine, threonine, methionine, cystine, asparagine, glutamine, aspartic acid, glutamic acid, tyrosine, cysteine, histidine, lysine, arginine, hydroxyproline and hydroxylysine), which are nutrients and may be used as dietary suppliments, to treat amino acid deficiencies or as penetration enhancers in cosmetic formulations; penicillamine, a chelating agent used to reduce cysteine excretion in cystinuria as well as in the treatment of rheumatoid arthritis; p-aminosalicylic acid, an antitubercular; p-aminobenzoic acid, an antirickettsial agent, a sunscreen, and also a local anesthetic when in esterified form; 4-amino-3-phenylbutyric acid, a mood elevator and tranquilizer; glutathione, for treating complications from overdoses of drugs or trace minerals; pangamic acid (Vitamin $B_{15}$), for vitamin deficiency or dietary supplement; chlorambucil, an antineoplastic; 4-(dimethylamino)benzoic acid, a sunscreen; baclofen, a muscle relaxant; benzmalecene, an anticholesteremic and gout suppressant; p-(benzylsulfonamido)benzoic acid, an adjunct in penicillin therapy; capobenic acid, an antiarrhythmic; furosemide, a diuretic and antihypertensive; pantothenic acid, a member of the B vitamin complex and dietary essential, useful as a dietary supplement or in treating vitamin deficiency; and probenecid, a uricosuric agent. However, the foregoing list is intended to be merely illustrative and in no way limitative of the types of utilities or of the particular compounds encompassed by this group.

Another group of parent acids from which compounds of the present invention can be considered to be derived consists of bio-affecting aromatic heterocycles of one, two, three or more rings which possess the requisite carboxylic acid group located either directly on a ring or as part of a side chain), e.g. pyridines, pteridines, naphthridines, pyrimidines, purines, and the like, as well as the corresponding partially or completely saturated heterocycles. One, two or more hetero atoms (N, S or O), which can be the same or different, can be present in each heterocyclic ring; however, carbocyclic rings (e.g. cyclohexane, benzene etc.) can also be present, just so long as there is at least one ring which contains at least one hetero ring atom. Illustrative members of this group of bioaffecting acids include methotrexate, an antineoplastic and antimetabolite; arecaidine, a miotic, anthelmintic or parasympathomimetic agent; nalidixic acid, an antibacterial agent which can be used to treat urocystitis; nicotinic acid (niacin), the enzyme cofactor vitamin, useful as a dietary supplement and in treatment of vitamin deficiency, e.g. for prevention and treatment of a pellagra-like disease in dogs; 9-xanthenecarboxylic acid, an anticholinergic in esterified form; folic acid, the hematopoietic vitamin, useful as a dietary supplement or to treat megaloblastic anemias; folinic acid, useful as an antidote for folic acid antagonists; lysergic acid, a psychomimetic drug; orotic acid, a uricosuric; 1-theobromineacetic acid, a diuretic, smooth muscle relaxant, cardiac stimulant and vasodilator; 7-theophyllineacetic acid, a diuretic, cardiac stimulant and smooth muscle relaxant; biotin, the growth factor, useful in preventing the biotin deficiency syndrome; mycophenolic acid, an antineoplastic agent; thioctic acid, useful in the treatment of liver disease and in the treatment of Amanita poisoning; and pyroglutamic acid, a moisturizing agent useful in cosmetic preparations. Of course, this list is not intended to be exhaustive as to utilities or compounds in this group.

Still another significant group of bio-affecting acids whose members can be derivatized according to the present invention comprises prostaglandins (derivatives of prostanoic acid), their precursors, their metabolites and structurally related synthetic compounds. Especially noteworthy members of this group include prostaglandins such as $PGE_1$ and $PGF_{2\alpha}$, which are abortifacients and smooth muscle stimulants, and $PGE_2$, which is an abortifacient, smooth muscle stimulant and vasodilator; thromboxanes, such as thromboxane $A_2$ ($TXA_2$), which promotes aggregation of platelets and constricts smooth muscle; and prostacyclin ($PGI_2$), which inhibits aggregation and relaxes smooth muscle. The thromboxanes and prostacyclins are of interest in controlling blood pressure, atherosclerosis, stroke and heart disease. Other group members and utilities will be apparent to the skilled artisan.

Another group of parent bio-affecting carboxylic acids comprises carbocylic ring systems, such as steroids or bicyclic terpene hydrocarbons. By way of example only, such parent acids include cephalosporin $P_1$, an antibiotic; cholic acid, a choleretic agent; fusidic acid, an antibiotic; and felogen, a choleretic. Among the steroids encompassed by this group, a particularly preferred class of parent acids, useful as anti-inflammatory agents when esterified at the 21-position, comprises compounds of the formula

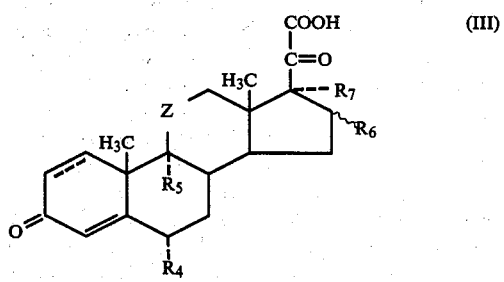

wherein $R_4$ is hydrogen, fluoro, chloro or methyl; $R_5$ is hydrogen, fluoro or chloro; $R_6$ is hydrogen, methyl, hydroxy or —$OCOR_8$ wherein $R_8$ is $C_1$–$C_7$ straight or branched alkyl or phenyl; $R_7$ is hydrogen, hydroxy or —$OCOR_8$ wherein $R_8$ is as defined above, with the proviso that when $R_6$ is hydroxy or —$OCOR_8$ and $R_7$ is other than hydrogen, then $R_6$ and $R_7$ are identical; or $R_6$ and $R_7$ are combined to form a divalent radical of the type

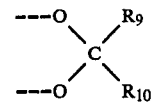

wherein $R_9$ and $R_{10}$, which can be the same or different, are each $C_1$–$C_7$ straight or branched alkyl or phenyl; Z is carbonyl or $\beta$-hydroxymethylene; the wavy line at the 16-position indicates the $\alpha$ or $\beta$-configuration; and the dotted line in ring A indicates that the 1,2-linkage is saturated or unsaturated. A particularly preferred group of carboxylic acids of formula (III) consists of the compounds wherein the structural variables represented by $R_4$, $R_5$, $R_6$, $R_7$ and Z and the dotted and wavy lines are identical to those of a known anti-inflammatory steroid selected from the group consisting of hydrocortisone, betamethasone, dexamethasone, prednisolone, triamcinolone, fluocortolone, cortisone, fludrocortisone, chloroprednisone, flumethasone, fluprednisolone, meprednisone, methyl prednisolone, paramethasone, prednisone, flurandrenolone acetonide, amcinafal, amcinafide, clocortolone, desonide, desoximetasone, difluprednate, flunisolide, fluocinolone acetonide, triamicolone acetonide, betamethasone 17-benzoate and betamethasone 17-valerate. Another preferred group of compounds of formula (III) consists of the compounds wherein the structural variables represented by $R_4$, $R_5$, $R_6$, Z and the dotted and wavy lines are identical to those of a known anti-inflammatory steroid selected from the group consisting of hydrocortisone, cortisone, fludrocortisone, betamethasone, chloroprednisone, dexamethasone, flumethasone, fluprednisolone, meprednisone, methyl prednisolone, paramethasone and prednisolone, and $R_7$ is —$OCOR_8$ wherein $R_8$ is as hereinbefore defined, most especially when $R_8$ is $CH_3$, $C_2H_5$, $C_3H_7$ or phenyl. Yet another preferred group of parent acids of formula (III) consists the compounds wherein the structural variables represented by $R_4$, $R_5$, Z and the wavy and dotted lines are identical to those of triamcinolone, and $R_6$ and $R_7$ are identical —$OCOR_8$ groupings wherein $R_8$ is as hereinbefore defined, most especially when $R_8$ is $CH_3$, $C_2H_5$, $C_3H_7$ or phenyl. Particularly preferred parent acids encompassed by formula (III) include 6$\alpha$-fluoro-11$\beta$-hydroxy-16$\alpha$-methyl-3,20-dioxopregna-1,4-dien-21-oic acid; 9$\alpha$-fluoro-11$\beta$,17$\alpha$-dihydroxy-16$\beta$-methyl-3,20-dioxopregna-1,4-dien-21-oic acid; 9$\alpha$-fluoro-11$\beta$,17$\alpha$-dihydroxy-16$\alpha$-methyl-3,20-dioxopregna-1,4-dien-21-oic acid; 11$\beta$,17$\alpha$-dihydroxy-3,20-dioxopregn-4-en-21-oic acid; 9$\alpha$-fluoro-11$\beta$,16$\alpha$,17$\alpha$-trihydroxy-3,20-dioxopregna-1,4-dien-21-oic acid; and 11$\beta$,17$\alpha$-dihydroxy-3,20-dioxopregna-1,4-dien-21-oic acid; as well as the corresponding 17-esters of the specific 17-hydroxy compounds just named, most especially the 17-propionates, butyrates and benzoates thereof.

Other parent carboxylic acids which can be derivatized according to the present invention include saturated and unsaturated aliphatic compounds (optionally containing hetero atoms), compounds containing cycloalkane or cycloalkene rings, and compounds containing one or more benzene rings (wherein the carboxylic acid group is attached either directly to the ring or to a side-chain). By way of illustration only, one can mention p-anisic acid, a local antiseptic and antirheumatic;

o-(p-anisoyl)benzoic acid, a hypoglycemic agent; camphoric acid, a central respiratory stimulant; caprochlorone, an antiviral; valproic acid, an anticonvulsant and antiepileptic; clofibric acid, for use in atherosclerosis, or as a hypolipemic or anticholesteremic agent; ethacrynamic acid, a diuretic; long chain fatty acids, synthetic or of natural origin, saturated or unsaturated, such as oleic, linoleic and arachidonic acids, as nutrients, emollients or penetration enhancers, topically as well as orally; phenoxyacetic acid, a fungicide and keratin exfoliative, chrysanthemic acid, a pesticide; retinoic acid, a keratolytic; 3,3'-thiodipropionic acid, an antioxidant in foods or cosmetics; tiglic acid and angelic acid, as sedatives; (2,4,5-trichlorophenoxy)acetic acid, a herbicide; vanillic and veratric acids, in cosmetic formulations; ascorbic acid (ring opened form), as a dietary supplement and for vitamin C deficiency, or as an antioxidant; lactic, pyruvic and other Krebs cycle carboxylic acids (e.g. cisaconitic acid, d-isocitric acid, α-ketoglutaric acid, succinic acid, fumaric acid, malic acid and oxaloacetic acid, as emollients and penetration enhancers, topically as well as orally; and benzilic acid, α-cyclopentyl-α-phenylacetic acid, 1-phenylcyclopentanecarboxylic acid, atrolactic acid, and α-phenyl-α-(2-thienyl)glycolic acid, which are anticholinergics or tranquilizers when in esterified form).

While all of the compounds encompassed by formulas (I) and (II) and their salts and N-oxides essentially satisfy the objectives of the present invention, preferred compounds include those derived from indomethacin, aspirin, naproxen, sulindac, ibuprofen, diflunisal, mefenamic acid, cefmetazole, cefazolin, cephalexin, ampicillin, amoxicillin, penicillin V, hetacillin, GABA, captopril, p-aminobenzoic acid, carbidopa, methyldopa, thyroxine, methotrexate, levodopa, valproic acid, chlorambucil, 4-(dimethylamino)benzoic acid, cholic acid, clofibric acid, fusidic acid, linoleic acid, mycophenolic acid, oleic acid, PGE$_1$, PGE$_2$, PGF$_{2\alpha}$, TXA$_2$, PGI$_2$, retinoic acid, 7-theophyllineacetic acid, 6α-fluoro-11β-hydroxy-16α-methyl-3,20-dioxopregna-1,4-dien-21-oic acid, 9α-fluoro-11β,17α-dihydroxy-16β-methyl-3,20-dioxopregna-1,4-dien-21-oic acid, 9α-fluoro-11β,17α-dihydroxy-16α-methyl-3,20-dioxopregna-1,4-dien-21-oic acid, 11β,17α-dihydroxy-3,20-dioxopregn-4-en-21-oic acid, 9α-fluoro-11β,16α,17α-trihydroxy-3,20-dioxopregna-1,4-dien-21-oic acid, and 11β,17α-dihydroxy-3,20-dioxopregna-1,4-dien-21-oic acid. Particularly preferred compounds of the invention include those wherein R—COO— or —OOC—R'—COO— is derived from one of the specific bio-affecting acids named in the preceding sentence, n is zero, R$_3$ is hydrogen,

wherein R$_1$' is C$_1$–C$_{10}$ alkyl or C$_6$–C$_{10}$ aryl, or R$_3$ is

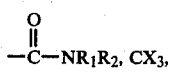

2-pyridyl, or 4-pyridyl, and R$_1$, R$_2$ and —NR$_1$R$_2$ are as defined hereinabove, especially when R$_3$ is hydrogen, and most especially when —NR$_1$R$_2$ represents the residue of an unsaturated heterocycle (such as imidazole, pyrazole and pyrrole); or when one of R$_1$ and R$_2$ is methyl and the other is phenyl or 2,4,6-trimethylphenyl; or when R$_1$ and R$_2$ are each lower alkyl such as methyl or ethyl, or —NR$_1$R$_2$ is morpholino or 4-methyl-1-piperazinyl or similar optionally substituted saturated heterocyclic, provided that the compounds in which —NR$_1$R$_2$ is dialkylamino or saturated heterocyclic are in the form of their N-oxides. Especially preferred species are described in the Examples hereinafter.

The compounds of the present invention can be prepared by a variety of synthetic routes, the method of choice depending upon the particular end product desired. One generally applicable process comprises reacting an alcohol of the formula

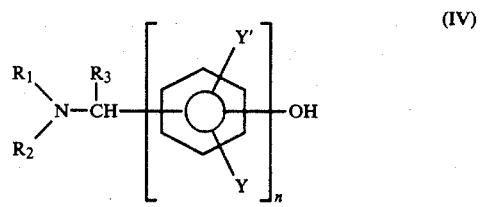

wherein R$_1$, R$_2$, NR$_1$R$_2$, R$_3$, Y, Y' and n are defined as hereinabove, with the parent acid or the corresponding acid chloride of the desired compound of formula (I) or (II), followed by, if desired, forming the corresponding salt or N-oxide as described hereinabove. Thus, the compounds of formula (I) are prepared by reacting the selected alcohol of formula (IV) with an acid of the formula

R—COOH                                    (V)

wherein R is defined as before, or with an acid chloride of the formula

R—COCl                                    (VI)

wherein R is defined as before. Similarly, the compounds of formula (II) are prepared by reacting the selected alcohol of formula (IV) with a dicarboxylic acid of the formula

HOOC—R'—COOH                              (VII)

wherein R' is defined as before, or with the corresponding acid chloride, i.e.

ClOC—R'—COCl                              (VIII)

wherein R' is defined as before. Obviously, in the latter case, two equivalents of alcohol will be reacted with each equivalent of diacid or di(acid chloride). Also, when an acid starting material is employed, i.e., a compound of formula (V) or (VII), then the reaction is conducted in the presence of a suitable dehydrating agent, for example dicyclohexylcarbodiimide, dimethylformamide dimethyl acetal or the like. The reaction is conveniently conducted in an inert solvent, such as dichloromethane, dioxane, ether, ethyl acetate or the like, at a temperature of from room temperature to reflux, for from 1 to 16 hours. When dicyclohexylcarbodiimide is used, the urea that precipitates is removed by filtration, the filtrate is concentrated and the concentrate is purified by conventional means to afford the desired compound of the invention.

The acid chlorides of formulas (VI) and (VIII) which can be used in the above method are prepared from the corresponding acids by known means, e.g. by treatment of the acid with thionyl chloride.

While the basic method described above can be used to prepare any of the compounds of the invention, certain conditions and/or modifications therein are made in specific instances. Thus, for example, when n in the compounds of the invention is one, then the method of choice uses an acid starting material, i.e. a compound of formula (V) or (VII), for reaction with the alcohol of formula (IV). Alternatively, however, the alcohol of formula (IV) can be reacted with the trifluoroacetic acid mixed anhydride of the carboxylic acid (prepared by mixing equal amounts of trifluoroacetic anhydride with the carboxylic acid at 0° C.) at from 0° C. to room temperature for a period of time of from about 1 to 12 hours. The reaction mixture can then be dissolved in an inert solvent (e.g. dichloromethane, ether, etc.) and extracted with aqueous sodium carbonate. The inert solvent can then be evaporated to give the desired compound of formula (I) or (II) wherein n is one.

The basic synthetic method described hereinabove is also modified in the instances in which the desired product of formula (I) or (II) contains free amino (primary or secondary), hydroxy or thiol groupings which, if present in the acid or acid chloride starting material, would undergo undesired side reaction and/or would interfere with the desired course of the above-described acylation. In such cases, the alcohol of formula (IV) is reacted with an acid of the formula

R''-COOH          (IX)

or

HOOC-R'''-COOH          (X)

wherein R''—COO— is the (—OH and/or amino and-/or —SH protected)acyloxy residue of a bio-affecting (—OH and/or amino and/or —SH containing-)monocarboxylic acid, and —OOC—R'''—COO— is the (—OH and/or amino and/or —SH protected)-di(acyloxy) residue of a bioaffecting (—OH and/or amino and/or —SH containing)dicarboxylic acid. The hydroxy, amino and thiol functions in the parent acids of formulas (V) and (VII), respectively, are converted to their protected counterparts in formulas (IX) and (X) by known methods, e.g. those known in the art of peptide synthesis. An especially desirable route to the protected acids of formulas (IX) and (X) comprises reacting the appropriate carboxylic acid of formula (V) or (VII) having other reactive functional groups such as —OH and —NH₂ with an excess of vinyl chloroformate (i.e.

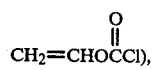

CH₂=CHOCCl), while maintaining the pH at between 7 and 8 (for example, using a pH stat), to give the completely protected acid wherein, for example, the H of the —OH group and one H of the —NH₂ group are replaced with vinylcarbonyloxy (—COOH=CH₂) units. [See Olofson et al, *Tetrahedron Letters*, 18, 1571-1574 (1977)]. When protected hydroxy and/or thiol groups as well as amino groups are present, the resultant protected acid can be converted to the corresponding intermediate containing free —OH and/or —SH groups, but vinylcarbonyloxy-protected amino groups, under mild hydrolysis conditions, e.g. by warming the completely protected acid with aqueous dioxane containing sodium carbonate. That partially deprotected intermediate can then be acylated, for example by reaction with

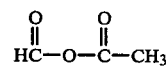

O    O
||   ||
HC—O—C—CH₃

(i.e., the mixed anhydride of acetic and formic acids, prepared by reaction of 2 parts by volume of acetic anhydride with 1 part by volume of 100% formic acid at 0° C.), to give a labile formate ester or thioester. Alternatively, more stable acyl groups, e.g. lower alkanoyl such as acetyl or pivaloyl, or benzoyl can be used, in which case the acyl group will be retained in the final product of formula (I) or (II).

Once the parent acid has been suitably protected as described above to give its protected counterpart of formula (IX) or (X), then that protected acid is reacted with the alcohol of formula (IV), in the presence of a suitable dehydrating agent, as described supra, to afford the compound corresponding to formula (I) or (II), but containing protected acyloxy residues, i.e. R''—COO— as defined above in place of R—COO— in formula (I) and —OOC—R'''—COO— as defined above in place of OCC—R'—COO— in formula (II). That protected compound can then be deprotected according to the method of Olofson et al, supra, by titrating the double bond with Br₂ in methanol (neutral conditions) to give the corresponding partially deprotected compound; i.e., the resultant compound, which is obtained as the hydrobromide salt, has free amino group(s), but the —OH and/or —SH functions are still protected by acyl functions. As explained above, if the acyl functions are stable, same can be retained and no further reaction is needed to afford the final bio-affecting product of formula (I) or (II), it being recognized however that the R—COO— or —OOC—R'—COO— grouping in said product differs from the corresponding grouping in the parent acid from which it was derived in that any free reactive —OH and/or —SH groups in the parent are lower alkanoyloxy or benzoyloxy and/or lower alkanoylthio or benzoylthio in the final product. Nevertheless, such partially protected acyloxy and di(acyloxy) residues are considered to be encompassed by the definitions of R—COO— and —OOC—R'—COO— as used herein.

On the other hand, if the acyl derivatives are unstable, i.e. when a labile formate ester or thioester grouping is present, same may be deprotected by the treatment with methanol; if necessary, however, the partially deprotected hydrobromide salt may then be treated with one equivalent of ammonia in methanol to afford the totally deprotected compound of formula (I) or (II). As an illustration of this process, the following reaction sequence is given, where the starting acid is the amino acid, tyrosine:

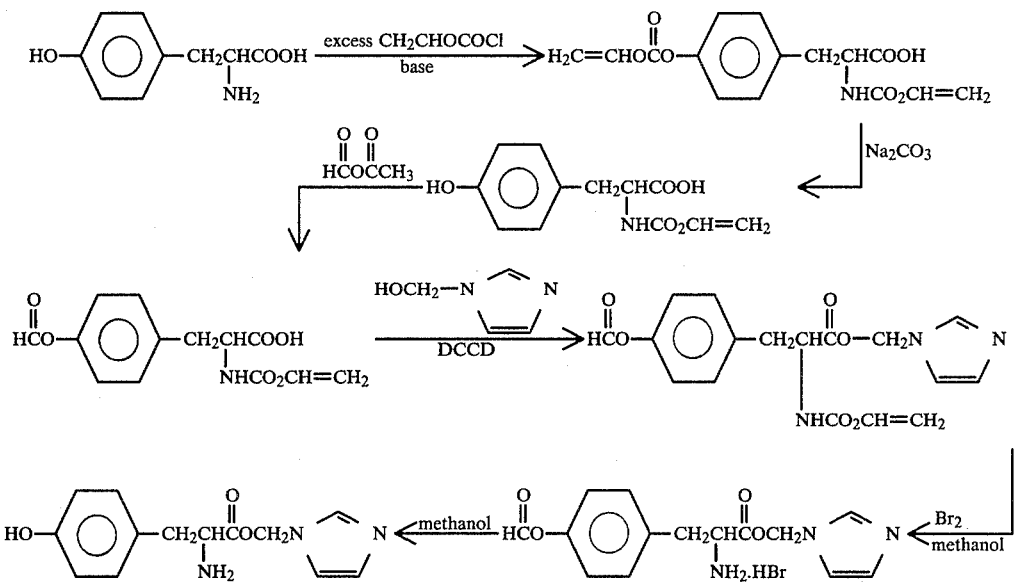

The above-described process variation involving the addition and ultimate removal of protecting groups is only used when the free amino, hydroxy and/or thiol functions are in need of protection. In some cases, for example in the case of the 11- and/or 16- and/or 17-hydroxysteroids encompassed by formula (III) hereinabove, the functional groups in question are not very reactive and would not need to be protected during the course of the reaction of the parent acid or its acid chloride with the alcohol of formula (IV).

The starting materials of formula (IV) wherein n is zero can be prepared by reacting one equivalent of an aldehyde of the formula

 (XI)

with one equivalent of the secondary amine

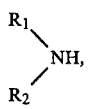 (XII)

neat or in an appropriate solvent.

When n is one, the starting materials of formula (IV) can be prepared by reacting the appropriate aldehyde of formula (XI), amine of formula (XII) and phenol of the formula

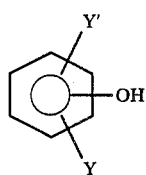 (XIII)

wherein Y and Y' are defined as above, according to the procedure of P. D. Gardner et al, *J. Am. Chem. Soc.*, 81, 3364 (1959). Thus, the selected phenol and aldehyde are mixed with the selected amine at from room temperature to 60° C. for from 1 to 12 hours, and the resultant compound of formula (IV) is obtained by crystallization from the reaction mixture or by extraction of the product with a water-immiscible solvent, e.g. dichloromethane, benzene, ether or the like, followed by evaporation. The primary product of this reaction can vary with the particular phenol employed. Thus, for example, use of 2,6-dimethylphenol principally affords compounds of the invention in which the acyloxy and —CH($R_3$)$NR_1R_2$ functions are located para to each other; in the case of using formaldehyde and dimethylamine as the other reactants, the resultant compound has the formula

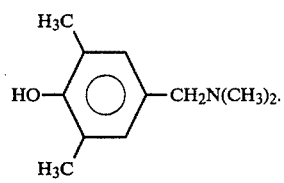

On the other hand, when phenol itself is used as a starting material, i.e. Y=Y'=H, then the product is primarily ortho-substituted; thus, in the case of the specific aldehyde and amine mentioned in the preceding sentence, the resultant alcohol of formula (IV) has the formula

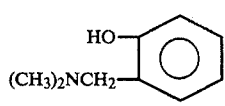

The compounds of the invention wherein n is zero, and wherein there are no functional groups requiring protection, can alternatively be prepared by reacting a compound of the formula

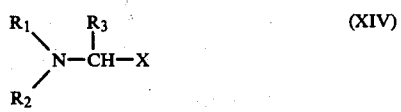

wherein $R_1$, $R_2$, $NR_1R_2$ and $R_3$ are defined as hereinabove and X is a suitable leaving group (e.g., halogen such as Cl or Br, or a methanesulfonyloxy or toluenesulfonyloxy group) with a carboxylic acid salt of the formula

or

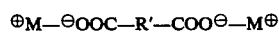

wherein RCOO— and —OOC—R'—COO— are defined as hereinabove and $M^\oplus$ is a suitable basic cation (e.g. sodium, potassium, thallium, triethylamine etc.). Typically, the formula (XIV) reactant is suspended in a suitable inert solvent such as dichloromethane, chloroform, tetrahydrofuran or the like, and reacted with the selected salt for from 3 to 16 hours at from room temperature to 60° C. The suspension is then filtered and the filtrate is evaporated to give the corresponding compound of formula (I) or (II) which can be purified by conventional means or, where the basic ester is insufficiently stable for conventional means, by converting the ester to its N-oxide or acid addition salt, as described hereinabove. Obviously, when a formula (XVI) reactant is used, 2 moles of amine are required per mole of salt.

The formula (XV) and (XVI) starting materials used in the above procedure are prepared from the corresponding monocarboxylic and dicarboxylic acids, respectively, by treatment with base, e.g. sodium hydroxide. The formula (XIV) starting materials are prepared by a reaction scheme which begins by reacting one equivalent of a selected aldehyde of formula (XI) above, e.g. an aqueous 37% formaldehyde solution, with two equivalents of an appropriate secondary amine of formula (XII) above, to give the corresponding bis(disubstitutedamino)methane of the formula

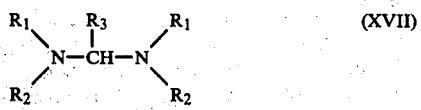

wherein $R_1$, $R_2$, $NR_1R_2$ and $R_3$ are defined as before. In accord with this process, after mixing the reactants, the solution is made basic with an inorganic base such as potassium hydroxide, sodium hydroxide or the like. The organic layer that separates is dried over potassium hydroxide and distilled. If the product is water soluble, the basicified solution is extracted with an inert, water-immiscible solvent such as ether, dichloromethane, etc., and the organic layer is dried over sodium sulfate and concentrated. The concentrate is then distilled to give the desired product. The resultant bis(disubstitutedamino)methane of formula (XVII) is then dissolved in an inert solvent such as ether, benzene, or the like. The solution is cooled and an acid chloride such as benzoyl chloride, bromide or iodide in the same inert solvent is added. The reaction is allowed to proceed at from 0° C. to room temperature for from one to sixteen hours, then the solution is filtered to give the appropriate disubstitutedaminomethyl halide of formula (XIV) where the identity of the halide depends on the acid halide used. If desired, that halide can then be subjected to an exchange reaction to afford the formula (XIV) reactants where X is a different leaving group, such as the tosylate or mesylate, for example, by reaction of the halide with the sodium salt of p-toluenesulfonic acid or the like.

The halides of formula (XIV) can also be prepared by reacting an alcohol of formula (IV) wherein n is zero with a halogenating agent such as thionyl chloride, oxalyl bromide, phosphorous oxychloride, etc. in an inert solvent such as dichloromethane, ether, benzene or the like, at from 0° to 60° C. for from one to eight hours to give the formula (XIV) halide either as an insoluble precipitate or by concentrating the solvent to dryness.

Yet another method for the preparation of compounds of formulas (I) and (II) wherein n is zero and wherein there are no functional groups which require protection comprises reacting a carboxylic acid halomethyl ester or similar compound of the formula

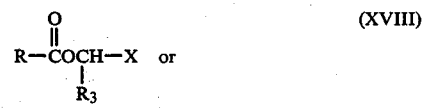

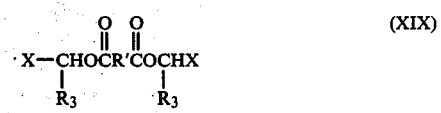

wherein R, R', $R_3$ and X are defined as hereinabove, with two or four equivalents, respectively, of a secondary amine of formula (XII), in an inert solvent such as dichloromethane, benzene, toluene or the like, at a temperature of from room temperature to reflux for from one to sixteen hours. The resultant suspension is filtered, the filtrate is concentrated, and the concentrate containing the corresponding compound of formula (I) or (II) is then purified by conventional means or converted to its N-oxide or salt.

The starting materials of formulas (XVIII) and (XIX) are prepared by first reacting the corresponding acid of formula (V) or (VII) with thionyl chloride or the like to afford the corresponding acid chloride of formula (VI) or (VIII), and then reacting that acid halide with an aldehyde of formula (XI), in the presence of an acid catalyst such as zinc chloride, to afford the corresponding chloride of formula (XVIII) or (XIX). That chloride can then be subjected to an exchange reaction to give the compounds in which X is a different leaving group.

When the starting acid of formula (V) is a steroidal acid of formula (III), same can be prepared by methods known in the art, for example by the methods described in U.S. Pat. No. 4,164,504 (Varma). See also *Chemical Abstracts*, 83, 179407 and 84, 122146. Thus, the following reaction scheme is illustrative of a general method for preparing the desired acids:

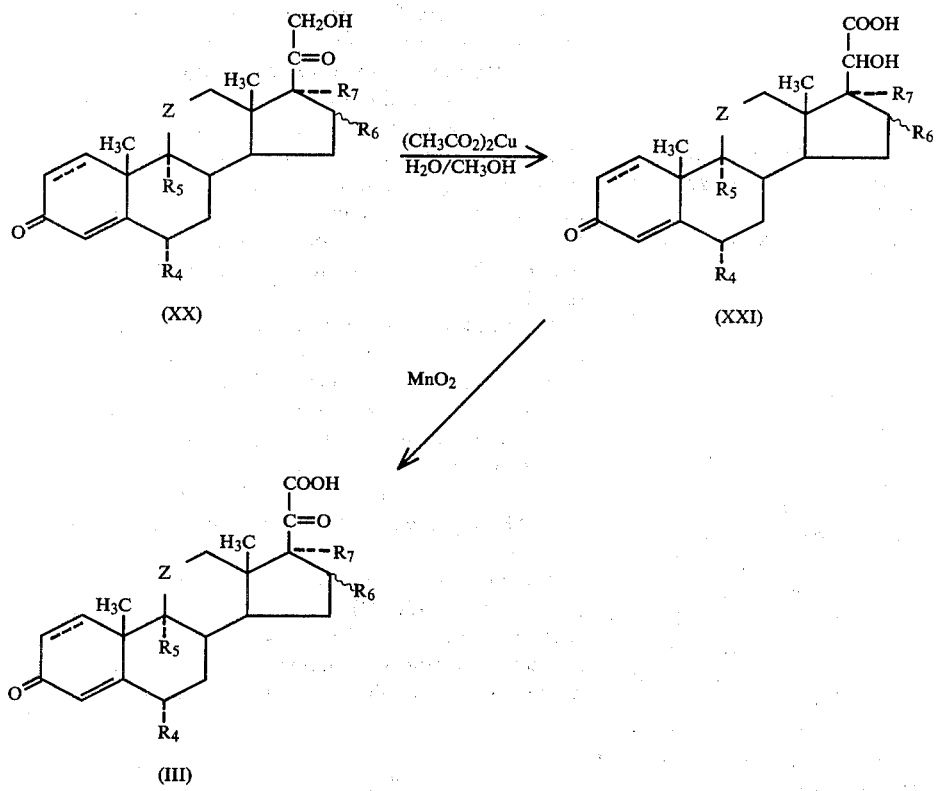

wherein R$_4$, R$_5$, R$_6$, R$_7$, Z and the dotted and wavy lines are defined as before. In the cupric acetate reaction, water is used as a co-solvent with a suitable alcohol, e.g. methanol or other lower alkanol, and the reaction is allowed to proceed for an extended period of time (more than 24 hours), since decreasing the water present and lessening reaction time tend to favor formation of the 21-ester of the steroid with the alcohol employed. Also, oxygen or air is bubbled through the mixture during the course of the reaction to encourage formation of 21-acid rather than 21-aldehyde. In the second step, the 20-hydroxy group is oxidized to a 20-keto function by reacting the steroid of formula (XXI) with manganese dioxide or lead dioxide in a inert halogenated hydrocarbon solvent such as chloroform or dichloromethane.

It will be appreciated that the compounds according to the present invention exhibit all of the biological and therapeutic activity of their "parent" drug species, for the treatment of whatever disease state or condition is known to be responsive to administration of the parent acid or its esters, at the same time being characterized by enhanced biphasic solubility, bioavailability and stability under acidic conditions, while at the same time being less irritating and more permeable through biological membranes and being characterized by being easily cleaved in vivo to essentially non-toxic moieties after achieving their desired therapeutic or other desired bioaffecting role.

The dose of the instant compound administered, whether orally, topically, intravenous solution, or the like, and whether a single dose or a daily dose, will, of course, vary with the size and needs of the individual, the identity of the compound and the condition for which it is administered. Moreover, the dosage administered is not subject to definite bounds, but will usually be an effective amount, or the equivalent on a molar basis of the pharmacologically active form produced upon the metabolic release of the active, parent acid to achieve its desired and physiological effect, for example, depending on the nature of the parent drug, an anti-inflammatory effective amount, an analgesic effective amount, an antipyretic effective amount, an antibiotic effective amount, an antihypertensive effective amount, etc. of the selected compound. See *Physicians' Desk Reference*, 31 (1977). Moreover, for any of the broad spectrum of dosage forms into which the subject soft drugs can be formulated, i.e., any of the dosage forms into which the parent acids can be formulated, see *Remington's Pharmaceutical Sciences*, 14th Edition (1970). Likewise, for those compounds of the invention derived from parent acids which are not used as pharmaceuticals but are otherwise bio-affecting, e.g., the sunscreens, dietary supplements or any of the other bio-affecting non-pharmaceutical acids, same can be formulated into any of the well-known compositions into which the parent acids or their esters are formulated and can be used for the same purposes.

The pharmaceutically active compounds of the present invention are conveniently administered to warm-blooded animals via conventional administration, most conveniently by combining the selected compound with any suitable non-toxic pharmaceutically acceptable inert carrier material. Such carrier materials are well known to those skilled in the art of pharmaceutical formulations. For those not skilled in the art, reference is made to the text entitled, "REMINGTON'S PHARMACEUTICAL SCIENCES" (Fourteenth Edition), 1970. In a typical preparation for oral administration, e.g., tablet or capsule, (e.g., as an anti-inflammatory or antibiotic) one of the orally effective compounds of the instant invention is combined in an effective amount with any suitable oral non-toxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citris pulp, carboxymethylcellulose and sodium lauryl sulfate. If desired, a conventional pharmaceutically acceptable dye can be incorporated into the dosage unit form, i.e., any of the standard FD&C dyes.

Similarly, in a typical formulation for topical application, e.g. as an anti-inflammatory agent, any one of the compounds of the instant invention which exhibits such activity topically is combined with a topical vehicle such as triacetin, such that the active ingredient is present in an effective amount. The preparation is simply applied topically to the inflamed area, whereby the therapeutically active compound is dermally absorbed at the site of inflammation.

Without further elaboration, it is believed that one of ordinary skill in the art can, using the preceding description, utilize the present invention to its fullest extent. Therefore, the following examples are to be construed as merely illustrative and not limitative of the remainder of the specification and claims in any way whatsoever.

EXAMPLE 1

Preparation of 1-(Hydroxymethyl)pyrazole

5 G of pyrazole were dissolved in 40 mL of 20% of hydrochloric acid, 15 mL of an aqueous solution of 30% formaldehyde were added, and the reaction mixture was agitated overnight at room temperature. The solution was then made basic with sodium hydroxide solution and extracted with ether, and the ether phase was dried over anhydrous sodium sulfate and evaporated. The residue which solidified was recrystallized from a mixture of ether and petroleum ether, to afford 2.93 g of the desired 1-(hydroxymethyl)pyrazole (m.p. 84°-88° C., 47% yield) clear, colorless crystals; NMR (CDCl$_3$) δ 7.3-7.6 (m, 3, 2 N—C$\underline{H}$+O$\underline{H}$), 6.2 (m, 1, C—C$\underline{H}$—C), 5.48 (s, 2, —C$\underline{H}_2$O—).

EXAMPLE 2

Preparation of 1-(4'-Chlorobenzoyl)-5-methoxy-2-methylindole-3-acetic acid (1'-pyrazolyl)methyl ester To an ice-cold suspension of indomethacin acid chloride (3.73 g, 0.01 mole) in CH$_2$Cl$_2$ (100 mL), were added triethylamine (1.01 g, 0.01 mole) and 1-(hydroxymethyl)pyrazole (0.96 g, 0.01 mole) in quick succession. The reaction mixture was allowed to stir and warm to room temperature overnight. The mixture was filtered and the residue was briefly triturated with 100 mL of boiling ethyl ether, which was then filtered, while hot, by gravity into the original filtrate. The pooled filtrates were concentrated to 200 mL, then 100 mL of cyclohexane were added to the solution slowly, while maintaining the solution at the reflux temperature. The solution was concentrated to a final volume of 125 mL, then was allowed to cool and crystallize overnight. The crystals which formed were removed by filtration, with suction, and washed twice with hexanes to give 2.38 g (mp 125°-126° C., 54% yield) of the desired product: NMR (CDCl$_3$), δ 7.7-6.2 (m, 10, aromatic-H), 6.05 (s, 2, —OCH$_2$N—), 3.78 (s, 3, OCH$_3$), 3.34 (O=CCH$_2$—), 2.30 (s, 3, CCH$_3$); IR (KBr), 3000-2800 cm$^{-1}$ (w) (C—H), 1730 cm$^{-1}$ (s) (O—C=O), 1660 cm$^{-1}$ (s) (N—C=O).

Anal. Calcd for C$_{23}$H$_{20}$ClN$_3$O$_4$: C, 63.08; H, 4.60; N, 9.60. Found: C, 63.33; H, 4.71; N, 9.42.

The product can be represented by the structural formula:

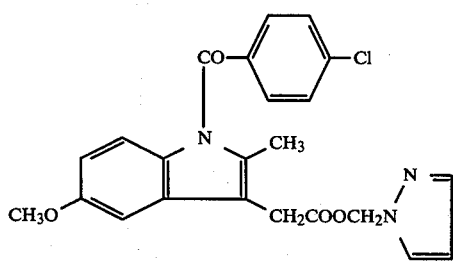

EXAMPLE 3

Preparation of 1-(2',2',2'-Trichloro-1'-hydroxy)ethylimidazole

To 5.65 g (0.038 mole) of anhydrous chloral was added a dichloromethane (40 mL) solution containing 2.58 g (0.038 mole) of imidazole. After 1 hour, the solution was concentrated in vacuo to give a foam. Crystallization from 200 mL of ether gave 3.43 g (mp 90°-96° C., 42% yield) of the desired compound. The mother liquor was concentrated to afford an additional 1.85 g of product identical with the first fraction: IR (KBr) 2900-1550 cm$^{-1}$, two very broad intense absorptions centered at 2400 and 1700 cm$^{-1}$; NMR (CDCl$_3$) δ7.76 (s, 1, N=C$\underline{H}$—N), 7.13 (s, 2, N—C$\underline{H}$=C$\underline{H}$—N), 7.0-7.5 (broad m, 0.8) and 11.7-11.3 (m, 1.2).

Anal. Calcd for C$_5$H$_5$Cl$_3$N$_2$O: C, 27.87; H, 2.34; N, 13.00. Found: C, 27.57; H, 2.49; N, 13.19.

The product has the formula:

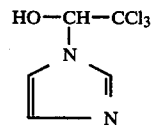

EXAMPLE 4

Preparation of 1-(4'-Chlorobenzoyl)-5-methoxy-2-methylindole-3-acetic acid 1-[2,2,2-trichloro-1-(1'-imidazolyl)]ethyl ester To 3.60 g (0.01 mole) of indomethacin dissolved in 100 mL of dichloromethane were added 2.1 g (0.01 mole) of dicyclohexylcarbodiimide and, after that solution became slightly turbid, 2.15 g (0.01 mole) of 1-(2',2',2'-trichloro-1'-hydroxy)ethylimidazole. The suspension that resulted was stirred at room temperature overnight, then was filtered. The filtrate was concentrated in vacuo to give 5.01 g of the desired compound as a yellow foam: $^1$H NMR (CDCl$_3$) δ7.73 (sharp m, 1, N=C$\underline{H}$—N), 6.91 (sharp m, 2, N—C$\underline{H}$=C$\underline{H}$—N), 7.53 (ABq, J=8 Hz, Δ$_{νAB}$=9 Hz, 4, aromatic-H), 7.2-6.5 (m, 3, aromatic-$\underline{H}$), 3.83 (s, 2, C$\underline{H}_2$—CO$_2$), 3.78 (s, 3, C$\underline{H}_3$—O) and 2.21 (s, 3, C$\underline{H}_3$—C).

The product has the structural formula:

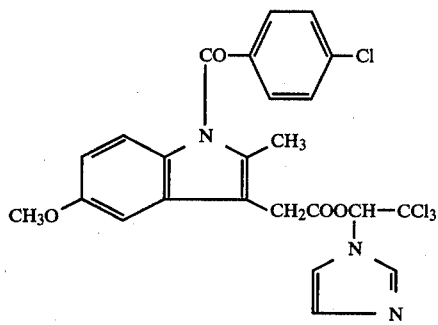

EXAMPLE 5

Preparation of Pivalic acid (1-imidazolyl)methyl ester

To 1.95 g (0.013 mole) of pivaloyloxymethyl chloride, dissolved in 20 ml of dichloromethane, were added 1.76 g (0.026 mole) of imidazole. The reaction mixture was refluxed for 32 hours, then was cooled and filtered. The filtrate was concentrated in vacuo to give an oil which was triturated with 100 mL of ether. The ether was decanted and concentrated in vacuo to give 1.30 g (55% yield) of the desired ester: IR (neat) 1720 cm$^{-1}$ (s) (C=O); NMR (CDCl$_3$) δ 7.7 (s, 1, N=C$\underline{H}$—N), 7.07 (s, 2, N—C$\underline{H}$=C$\underline{H}$—N), 5.9 (s, 2, N—CH$_2$—O$_2$C), and 1.17 (s, 9, (CH$_3$)$_3$C).

The product which can also be named 1-pivaloyloxymethyl imidazole, has the structural formula:

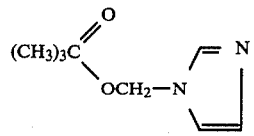

The following compounds of the invention are also prepared utilizing the processes generally or specifically described herein, for example, the methods of Examples 2, 4 or 5, or their obvious chemical equivalents. It should be noted that when the final products have free amino and/or hydroxy and/or thiol groups, those products are obtained by first forming the N- and/or O and/or S-protected derivatives of the parent acids as generally described hereinabove, preferably via the vinyl chloroformate route, then reacting those acids having protected amino, hydroxy and/or thiol functions with the appropriate alcohol of formula (IV) in the presence of a suitable dehydrating agent (e.g. as described in Example 4), and then removing the protecting groups as generally described hereinabove to afford the desired compounds of the invention. Also, as will be obvious to those skilled in the art, the amounts of reactants used will depend on whether the compound is derived from an acid having 1 or 2 carboxylic acid groups. Where indicated, the compounds are subsequently converted to N-oxides as generally described hereinabove.

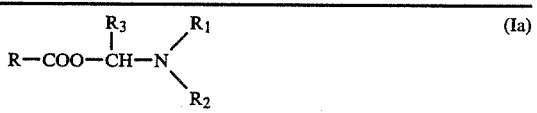

| Example Number | R—COO— is the mono-acyloxy residue of | R$_3$ | $-N\begin{smallmatrix}R_1\\R_2\end{smallmatrix}$ |
|---|---|---|---|
| 6 | indomethacin | H | 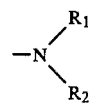 |
| 7 | indomethacin | CCl$_3$ | 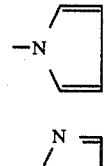 |
| 8 | indomethacin | CCl$_3$ | 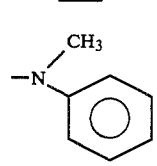 |
| 9 | indomethacin | H | 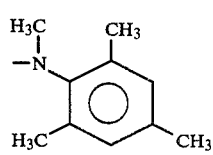 |

| | | | |
|---|---|---|---|
| 10 | indomethacin | H | 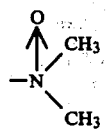 |
| 11 | indomethacin | H | 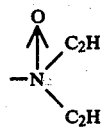 |
| 12 | indomethacin | H | 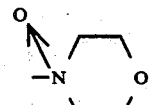 |
| 13 | indomethacin | H | 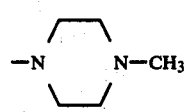 |
| 14 | indomethacin | H | 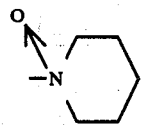 |
| 15 | indomethacin | H | 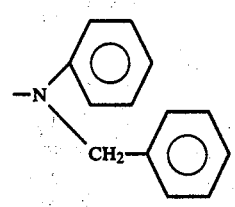 |
| 16 | indomethacin | H | 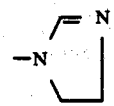 |
| 17 | indomethacin | CCl$_3$ | 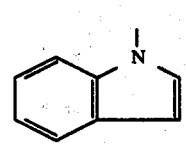 |
| 18 | indomethacin | H | 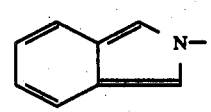 |
| 19 | indomethacin | H | 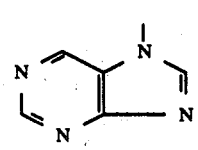 |
| 20 | indomethacin | $-\overset{\text{O}}{\underset{\|}{\text{C}}}-\text{CH}_3$ | 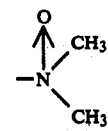 |

-continued

| # | Drug | R | Heterocycle |
|---|---|---|---|
| 21 | indomethacin | −C(=O)−C₆H₅ | −N(N=CH−CH=CH) (imidazole) |
| 22 | indomethacin | −C(=O)−N(CH₃)₂ | −N(N=CH−CH=CH) (imidazole) |
| 23 | indomethacin | 2-pyridyl | −N(N=CH−CH=CH) (imidazole) |
| 24 | indomethacin | 4-pyridyl | −N(N=CH−CH=N) (pyrazole) |
| 25 | aspirin | H | −N(N=CH−CH=CH) (imidazole) |
| 26 | aspirin | CCl₃ | −N(N=CH−CH=CH) (imidazole) |
| 27 | naproxen | H | −N(N=CH−CH=CH) (imidazole) |
| 28 | naproxen | CCl₃ | −N(N=CH−CH=CH) (imidazole) |
| 29 | sulindac | H | −N(N=CH−CH=CH) (imidazole) |
| 30 | sulindac | 4-pyridyl | −N(N=CH−CH=CH) (imidazole) |
| 31 | ibuprofen | H | −N(N=CH−CH=CH) (imidazole) |
| 31a | ibuprofen | −C(=O)−CH₃ | −N(C₂H₅)₂→O (N,N-diethyl-N-oxide) |
| 32 | diflunisal | H | −N(N=CH−CH=CH) (imidazole) |

-continued

| | | | |
|---|---|---|---|
| 33 | diflunisal | CCl₃ | -N(CH₃)(2,4,6-trimethylphenyl) |
| 34 | aspirin | H | -N(CH₃)₂ C(=O) (N-oxide dimethylamide) |
| 35 | naproxen | H | -N(C₂H₅)₂ (N-oxide) |
| 36 | sulindac | H | -N(CH₃)(phenyl) |
| 37 | diflunisal | H | -N(CH₃)₂ (N-oxide) |
| 38 | mefenamic acid | H | -N(imidazolyl) |
| 39 | mefenamic acid | H | -N(CH₃)₂ (N-oxide) |
| 40 | fenoprofen | H | -N(imidazolyl) |
| 41 | tolmetin | H | -N(pyrazolyl) |
| 42 | flurbiprofen | CCl₃ | -N(CH₃)₂ (N-oxide) |
| 43 | indoprofen | H | -N(morpholinyl) (N-oxide) |
| 44 | fenclozic acid | H | -N(imidazolyl) |

-continued

| | | | |
|---|---|---|---|
| 45 | ketoprofen | H | -N(CH=N-CH=CH) imidazole |
| 46 | alclofenac | H | -N(CH=N-CH=CH) imidazole |
| 47 | bucloxic acid | $CCl_3$ | -N(CH₃)-(2,4,6-trimethylphenyl) |
| 48 | meclofenamic acid | H | -N(CH=N-CH=CH) imidazole |
| 49 | flufenamic acid | H | -N-N=CH-CH=CH pyrazole |
| 50 | cinchophen | H | -N(CH₃)₂ with O |
| 51 | voltaren | H | -N(CH=N-CH=CH) imidazole |
| 52 | cimetacin | H | -N(CH=N-CH=CH) imidazole |
| 53 | ibufenac | H | -N(CH=N-CH=CH) imidazole |
| 54 | furobufen | H | -N(CH₃)₂ with O |
| 55 | fenclofenac | H | -N(CH₃)-(2,4,6-trimethylphenyl) |
| 56 | prodolic acid | $CCl_3$ | -N(CH=N-CH=CH) imidazole |

-continued
| | | | |
|---|---|---|---|
| 57 | pirprofen | H |  |
| 58 | oxoprozin | H |  |
| 59 | clonixin | CCl₃ | 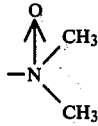 |
| 60 | fluprofen | H | 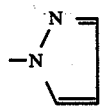 |
| 61 | flutiazin | H | 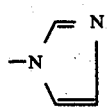 |
| 62 | salicylic acid | H | 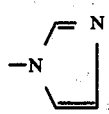 |
| 63 | niflumic acid | H | 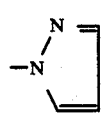 |
| 64 | clometacin | H | 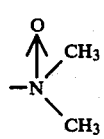 |
| 65 | flufenisal | H | 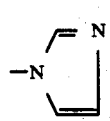 |
| 66 | salsalate | H | 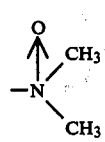 |
| 67 | flunixin | H | 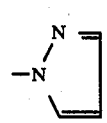 |
| 68 | cefmetazole | H | 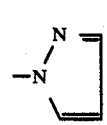 |
| 69 | cefmetazole | CCl₃ | 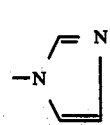 |

-continued
| # | Compound | R | Group |
|---|---|---|---|
| 70 | cefmetazole | H | 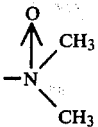 |
| 71 | cefazolin | 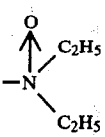 | 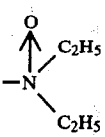 |
| 72 | cefazolin | —C(=O)—CH₃ | 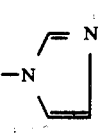 |
| 73 | cefazolin | —C(=O)—Ph | 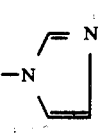 |
| 74 | cephalexin | H | 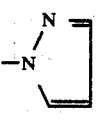 |
| 75 | cephalexin | CCl₃ | 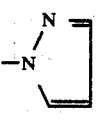 |
| 76 | cephalexin | H | 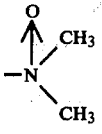 |
| 77 | ampicillin | H | 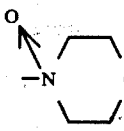 |
| 78 | ampicillin | CCl₃ | 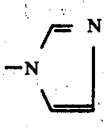 |
| 79 | ampicillin | —C(=O)—Ph | 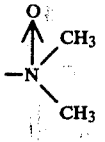 |
| 80 | amoxicillin | 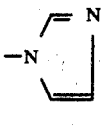 | 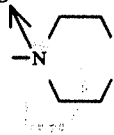 |
| 81 | amoxicillin | —C(=O)—CH₃ | 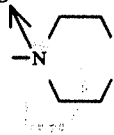 |

-continued
| 82 | amoxicillin | H | 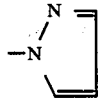 |
| 83 | penicillin V | H | 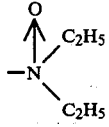 |
| 84 | penicillin V | H | 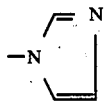 |
| 85 | penicillin V | H |  |
| 86 | hetacillin | H |  |
| 87 | hetacillin | CCl₃ | 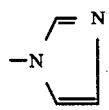 |
| 88 | hetacillin | H | 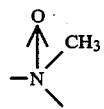 |
| 89 | GABA | H | 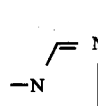 |
| 90 | GABA | H | 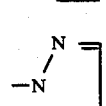 |
| 91 | GABA | CCl₃ | 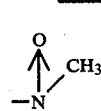 |
| 92 | captopril | CCl₃ | 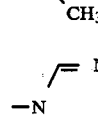 |
| 93 | captopril | H | 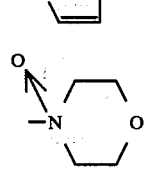 |
| 94 | captopril | H | 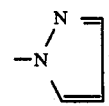 |

-continued

| # | Drug | R | Group |
|---|---|---|---|
| 95 | p-aminobenzoic acid | H | –N(O)(CH₃)₂ (N-oxide dimethyl) |
| 96 | p-aminobenzoic acid | –C(=O)CH₃ | imidazolyl |
| 97 | p-aminobenzoic acid | CCl₃ | pyrazolyl |
| 98 | carbidopa | H | pyrazolyl |
| 99 | carbidopa | CCl₃ | imidazolyl |
| 100 | carbidopa | –C(=O)–C₆H₅ | N-oxide dimethylamino |
| 101 | methyldopa | H | imidazolyl |
| 102 | methyldopa | 4-methylpyridyl | morpholino N-oxide |
| 103 | methyldopa | –C(=O)–N(CH₃)₂ | 2,4,6-trimethylanilino |
| 104 | thyroxine | H | imidazolyl |
| 105 | thyroxine | CCl₃ | pyrazolyl |
| 106 | thyroxine | H | –N(O)(CH₃)₂ |

-continued
| | | | |
|---|---|---|---|
| 107 | chlorambucil | H | 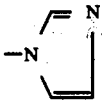 |
| 108 | chlorambucil | CCl₃ | 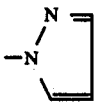 |
| 109 | chlorambucil | $-\underset{\underset{O}{\parallel}}{C}-CH_3$ | 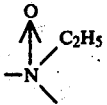 |
| 110 | 4-(dimethylamino)-benzoic acid | H | 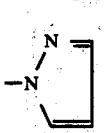 |
| 111 | 4-(dimethylamino)-benzoic acid | CCl₃ | 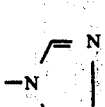 |
| 112 | 4-(dimethylamino)-benzoic acid | $-\underset{\underset{O}{\parallel}}{C}-CH_3$ | 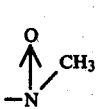 |
| 113 | levodopa | H | 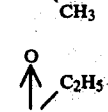 |
| 114 | levodopa | CCl₃ | 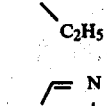 |
| 115 | levodopa | 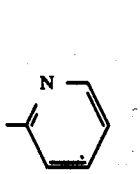 | 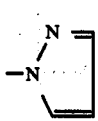 |
| 116 | glycine | H | 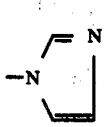 |
| 117 | leucine | CCl₃ | 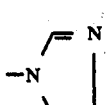 |
| 118 | phenylalanine | H | 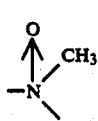 |
| 119 | aspartic acid | H | |

| # | Drug | R | Structure |
|---|---|---|---|
| 120 | tyrosine | CCl₃ | −N(→O)(C₂H₅)₂ |
| 121 | cysteine | H | −N(CH₃)-(2,4,6-trimethylphenyl) |
| 122 | valproic acid | H | −N-(imidazol-1-yl) |
| 123 | valproic acid | CCl₃ | −N-(pyrazol-1-yl) |
| 124 | valproic acid | 4-pyridyl | −N(→O)(CH₃)₂ |
| 125 | cholic acid | H | −N-(pyrazol-1-yl) |
| 126 | cholic acid | H | −N(→O)(C₂H₅)₂ |
| 127 | cholic acid | CCl₃ | −N-(imidazol-1-yl) |
| 128 | clofibric acid | H | −N-(imidazol-1-yl) |
| 129 | clofibric acid | H | −N-(pyrazol-1-yl) |
| 130 | clofibric acid | CCl₃ | −N(→O)(CH₃)(CH₂C₆H₅) |
| 131 | fusidic acid | H | −N-(pyrazol-1-yl) |

-continued

| | | | |
|---|---|---|---|
| 132 | fusidic acid | CCl₃ | imidazol-1-yl |
| 133 | fusidic acid | H | -N(→O)(C₂H₅)₂ |
| 134 | mycophenolic acid | H | pyrazol-1-yl |
| 135 | mycophenolic acid | CCl₃ | pyrazol-1-yl |
| 136 | mycophenolic acid | -C(=O)CH₃ | -N(→O)(CH₃)₂ |
| 137 | oleic acid | H | pyrazol-1-yl |
| 138 | oleic acid | CCl₃ | imidazol-1-yl |
| 139 | oleic acid | H | -N(→O)(CH₃)₂ |
| 140 | PGE₁ | H | pyrazol-1-yl |
| 141 | PGE₁ | CCl₃ | imidazol-1-yl |
| 142 | PGE₁ | -C(=O)CH₃ | -N(→O)(CH₃)₂ |
| 143 | PGE₂ | H | morpholine N-oxide |

| | | | |
|---|---|---|---|
| 144 | PGE₂ | CCl₃ | 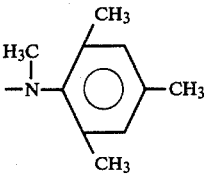 |
| 145 | PGE₂ | 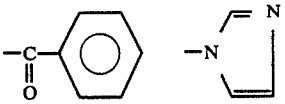 |  |
| 146 | PGF₂α | H |  |
| 147 | PGF₂α | CCl₃ | 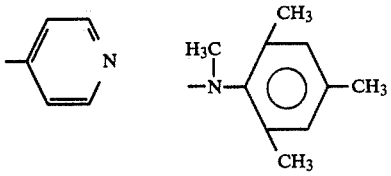 |
| 148 | PGF₂α | 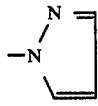 |  |
| 149 | TXA₂ | H | 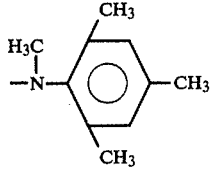 |
| 150 | TXA₂ | CCl₃ |  |
| 151 | TXA₂ | —C(=O)—CH₃ |  |
| 152 | PGI₂ | H | |
| 153 | PGI₂ | H | |
| 154 | PGI₂ | CCl₃ | 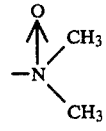 |
| 155 | retinoic acid | H |  |

-continued

| | | | |
|---|---|---|---|
| 156 | retinoic acid | CCl₃ | imidazole |
| 157 | retinoic acid | H | N(CH₃)₂→O |
| 158 | 7-theophyllineacetic acid | H | imidazole |
| 159 | 7-theophyllineacetic acid | CCl₃ | pyrazole |
| 160 | 7-theophyllineacetic acid | H | N(CH₃)(C₂H₅)→O |
| 161 | cefoxitin | H | imidazole |
| 162 | cephaloglycin | H | N(CH₃)(C₂H₅)→O |
| 163 | cephalosporin P₁ | CCl₃ | imidazole |
| 164 | cephalosporin C | H | imidazole |
| 165 | cephalothin | —C(=O)—C₆H₅ | pyrazole |
| 166 | cephamycin A | —C(=O)—C₆H₅ | N(CH₃)₂→O |
| 167 | cephamycin C | H | —N(CH₃)—(2,4,6-trimethylphenyl) |

| | | | |
|---|---|---|---|
| | | -continued | |
| 168 | cephamycin B | 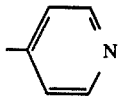 |  |
| 169 | carfecillin | CCl$_3$ | 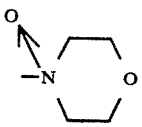 |
| 170 | amylpenicillin | H |  |
| 171 | clometacillin | H | 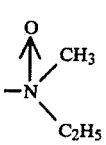 |
| 172 | cloxacillin | CCl$_3$ | 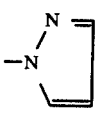 |
| 173 | methicillin | H | 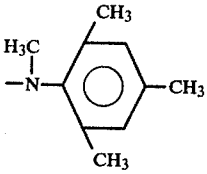 |
| 174 | penicillin O | —C(=O)—CH$_3$ | 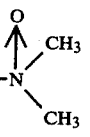 |
| 175 | chlorobutin penicillin | CCl$_3$ |  |
| 176 | diphenicillin | 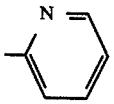 |  |
| 177 | metampicillin | 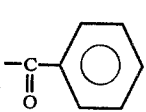 | 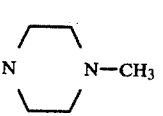 |
| 178 | benzilic acid | H |  |
| 179 | benzilic acid | CCl$_3$ | 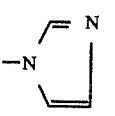 |

-continued

| | | | |
|---|---|---|---|
| 180 | benzilic acid | 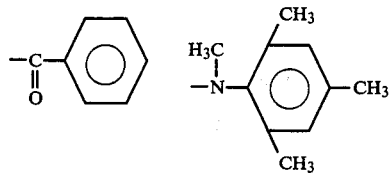 | |
| 181 | α-cyclopentyl-α-phenylacetic acid | —C(=O)—CH₃ | 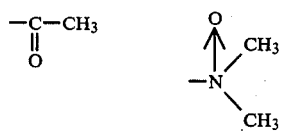 |
| 182 | α-cyclopentyl-α-phenylacetic acid | H |  |
| 183 | α-cyclopentyl-α-phenylacetic acid | 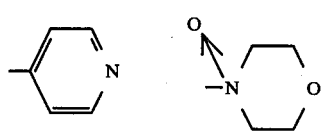 | |
| 184 | 1-phenylcyclopentane carboxylic acid | H | 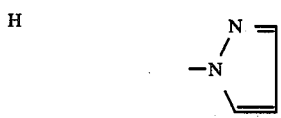 |
| 185 | 1-phenylcyclopentane carboxylic acid | H | 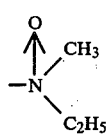 |
| 186 | 1-phenylcyclopentane carboxylic acid | CCl₃ | 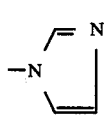 |
| 187 | atrolactic acid | H | 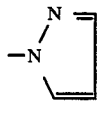 |
| 188 | atrolactic acid | 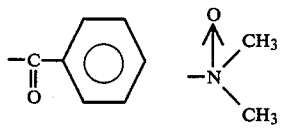 | |
| 189 | atrolactic acid | CCl₃ | 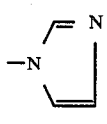 |
| 190 | α-phenyl-α-(2-thienyl)glycolic acid | H | 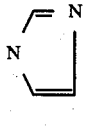 |
| 191 | α-phenyl-α-(2-thienyl)glycolic acid | CCl₃ | 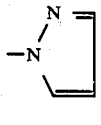 |

-continued

| | | | |
|---|---|---|---|
| 192 | α-phenyl-α-(2-thienyl)glycolic acid | H | 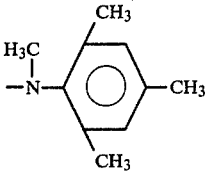 |
| 193 | 9-xanthenecarboxylic acid | H | 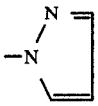 |
| 194 | 9-xanthenecarboxylic acid | CCl₃ | 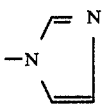 |
| 195 | 9-xanthenecarboxylic acid | H | 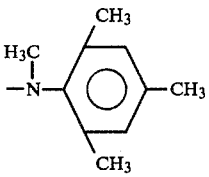 |
| 196 | 9-xanthenecarboxylic acid | —C(=O)—CH₃ | 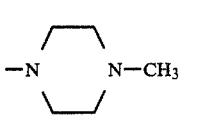 |
| 197 | 9-xanthenecarboxylic acid | 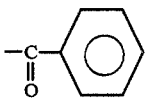 | 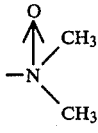 |
| 198 | 9-xanthenecarboxylic acid | 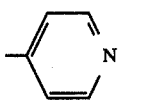 | 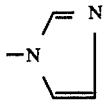 |

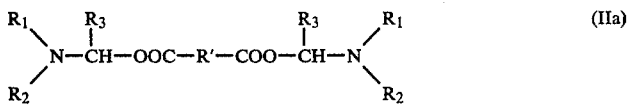

(IIa)

| Example Number | —OOC—R′—COO— is the di(acyloxy) residue of | $R_3$ | $-N\begin{matrix}R_1\\R_2\end{matrix}$ |
|---|---|---|---|
| 199 | methotrexate | H | 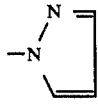 |
| 200 | methotrexate | CCl₃ | 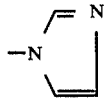 |
| 201 | methotrexate | H | 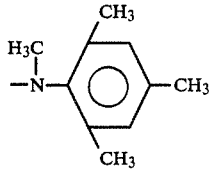 |

-continued

| | | | |
|---|---|---|---|
| 202 | methotrexate | −C(=O)−CH₃ | −N⁺(CH₃)₂→O |
| 203 | methotrexate | −C(=O)−C₆H₅ | −N⁺(morpholino)→O |
| 204 | methotrexate | −(4-pyridyl) | −N(imidazolyl) |
| 205 | carbenicillin | H | −N(pyrazolyl) |
| 206 | carbenicillin | H | −N(2,4,6-trimethylphenyl) |

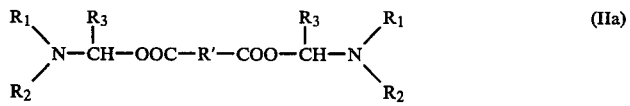
(IIa)

| Example Number | −OOC−R′−COO− is the di(acyloxy) residue of | R₃ | N(R₁)(R₂) |
|---|---|---|---|
| 207 | carbenicillin | −C(=O)−CH₃ | −N⁺(morpholino)→O |
| 208 | penicillin N | CCl₃ | −N(imidazolyl) |
| 209 | penicillin N | −C(=O)−C₆H₅ | −N⁺(CH₃)₂→O |
| 210 | penicillin N | −(4-pyridyl) | −N(imidazolyl) |
| 211 | glutathione | H | −N(imidazolyl) |

| | | | |
|---|---|---|---|
| 212 | glutathione | CCl₃ |  |
| 213 | glutathione | H | 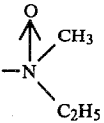 |
| 214 | glutathione | —C(=O)—CH₃ |  |
| 215 | glutathione | 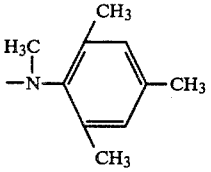 |  |
| 216 | glutathione |  |  |
| 217 | camphoric acid | H | 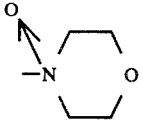 |
| 218 | camphoric acid | CCl₃ |  |
| 219 | camphoric acid | —C(=O)—CH₃ |  |
| 220 | fumaric acid | H |  |
| 221 | fumaric acid | CCl₃ | 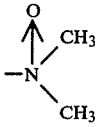 |
| 222 | fumaric acid | H |  |

The following compounds of the invention are prepared by reacting the corresponding acid with the appropriate alcohol of formula (IV) wherein n is 1 (which alcohol is prepared as generally described hereinabove), in the presence of a suitable dehydrating agent (e.g. dicyclohexylcarbodiimide), for example as described in Example 4, or by reacting the alcohol with the trifluoroacetic acid mixed anhydride of the carboxylic acid as generally described hereinabove.

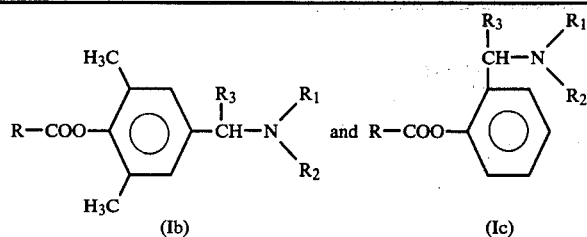

| Example Number | Formula | R—COO— is the mono-acyloxy residue of | $R_3$ | $-N\begin{smallmatrix}R_1\\R_2\end{smallmatrix}$ |
|---|---|---|---|---|
| 223 | Ib | indomethacin | H | pyrazol-1-yl |
| 224 | Ib | indomethacin | $CCl_3$ | imidazol-1-yl |
| 225 | Ic | indomethacin | H | N(CH₃)(2,4,6-trimethylphenyl) |
| 226 | Ic | indomethacin | —C(=O)—C₆H₅ | —N(O)(CH₃)₂ |
| 227 | Ib | aspirin | H | imidazol-1-yl |
| 228 | Ic | naproxen | $CCl_3$ | pyrazol-1-yl |
| 229 | Ic | sulindac | H | —N(O)(CH₃)₂ |
| 230 | Ib | ibuprofen | H | pyrazol-1-yl |
| 231 | Ic | diflunisal | $CCl_3$ | imidazol-1-yl |
| 232 | Ib | cefmetazole | H | pyrazol-1-yl |

-continued

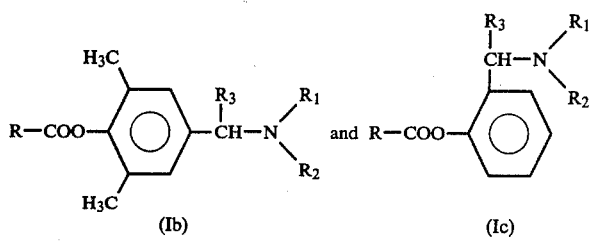

| Example Number | Formula | R—COO— is the monoacyloxy residue of | $R_3$ | $-N\begin{matrix}R_1\\R_2\end{matrix}$ |
|---|---|---|---|---|
| 233 | Ic | cefmetazole | $CCl_3$ | imidazol-1-yl |
| 234 | Ib | cefazolin | H | imidazol-1-yl |
| 235 | Ic | cefazolin | $CCl_3$ | $-N(CH_3)_2 \rightarrow O$ |
| 236 | Ib | cephalexin | H | pyrazol-1-yl |
| 237 | Ib | cephalexin | $CCl_3$ | imidazol-1-yl |
| 238 | Ic | cephalexin | $-C(=O)-C_6H_5$ | $-N(CH_3)(2,4,6\text{-trimethylphenyl})$ |
| 239 | Ic | cephalexin | 4-pyridyl | $-N(CH_3)(C_2H_5) \rightarrow O$ |
| 240 | Ib | ampicillin | $CCl_3$ | imidazol-1-yl |
| 241 | Ib | ampicillin | H | pyrazol-1-yl |

-continued

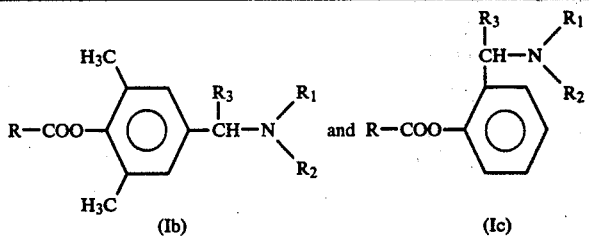

| Example Number | Formula | R—COO— is the mono-acyloxy residue of | R₃ | —N(R₁)(R₂) |
|---|---|---|---|---|
| 242 | Ic | ampicillin | $-\underset{\underset{O}{\parallel}}{C}-CH_3$ | N-mesityl (N-methyl-2,4,6-trimethylanilino) |
| 243 | Ic | ampicillin | 2-pyridyl | N,N-dimethyl N-oxide |
| 244 | Ib | amoxicillin | H | imidazol-1-yl |
| 245 | Ib | amoxicillin | $CCl_3$ | pyrazol-1-yl |
| 246 | Ic | amoxicillin | benzoyl | N,N-diethyl N-oxide |
| 247 | Ic | amoxicillin | 4-pyridyl | N-mesityl (N-methyl-2,4,6-trimethylanilino) |
| 248 | Ib | penicillin V | $CCl_3$ | imidazol-1-yl |
| 249 | Ic | penicillin V | H | pyrazol-1-yl |
| 250 | Ib | hetacillin | H | imidazol-1-yl |

-continued (Ib) structure: R—COO—(2,6-dimethylphenyl)—CH(R₃)—N(R₁)(R₂)

(Ic) structure: R—COO—(phenyl)—CH(R₃)—N(R₁)(R₂)

| Example Number | Formula | R—COO— is the mono-acyloxy residue of | $R_3$ | $-N\begin{subarray}{l}R_1\\R_2\end{subarray}$ |
|---|---|---|---|---|
| 251 | Ic | hetacillin | $-\overset{\text{O}}{\underset{\|}{C}}-CH_3$ | N(OCH₃)-(2,4,6-trimethylcyclohexyl) |
| 252 | Ic | GABA | H | pyrazol-1-yl |
| 253 | Ic | GABA | CCl₃ | imidazol-1-yl |
| 254 | Ib | captopril | H | imidazol-1-yl |
| 255 | Ic | captopril | CCl₃ | pyrazol-1-yl |
| 256 | Ib | carbidopa | H | imidazol-1-yl |
| 257 | Ic | carbidopa | $-\overset{\text{O}}{\underset{\|}{C}}-C_6H_5$ | pyrazol-1-yl |
| 258 | Ib | methyldopa | CCl₃ | N-(2,4,6-trimethylphenyl) |
| 259 | Ic | methyldopa | 4-pyridyl | $-N(\to O)(CH_3)_2$ |

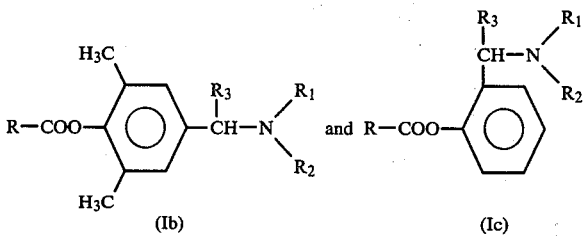

| Example Number | Formula | R—COO— is the monoacyloxy residue of | $R_3$ | $-N\begin{array}{c}R_1\\R_2\end{array}$ |
|---|---|---|---|---|
| 260 | Ib | thyroxine | H | pyrazolyl |
| 261 | Ic | thyroxine | $CCl_3$ | imidazolyl |
| 262 | Ib | levodopa | H | morpholino N-oxide |
| 263 | Ic | levodopa | $-\underset{\underset{O}{\parallel}}{C}-CH_3$ | imidazolyl |
| 264 | Ib | chlorambucil | H | pyrazolyl |
| 265 | Ic | chlorambucil | $CCl_3$ | imidazolyl |

The following compounds of the invention are also prepared utilizing the processes generally or specifically described herein, for example, the methods of Examples 2, 4 or 5, or their obvious chemical equivalents. For this group of compounds, the free hydroxy groups in the starting material [e.g. in the acid of formula (III)] are generally inert to the reaction conditions used and thus need not be protected during the acylation.

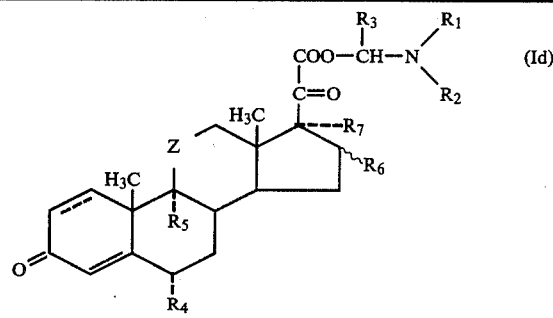

| Example Number | Δ¹ | R₄ | R₅ | Z | R₆ | R₇ | R₃ | -N(R₁)(R₂) |
|---|---|---|---|---|---|---|---|---|
| 266 | saturated | H | H | >C(H)(OH)- | H | OH | H | pyrazol-1-yl |
| 267 | saturated | H | H | >C(H)(OH)- | H | OH | $CCl_3$ | imidazol-1-yl |
| 268 | saturated | H | H | >C(H)(OH)- | H | OH | $-C(=O)CH_3$ | imidazol-1-yl |
| 269 | saturated | H | H | >C(H)(OH)- | H | OH | H | N-methyl-2,4,6-trimethylcyclohexylamino |
| 270 | saturated | H | H | >C(H)(OH)- | H | OH | 4-pyridyl | $-N(CH_3)_2 \to O$ |
| 271 | saturated | H | H | >C(H)(OH)- | H | OH | $-C(=O)C_6H_5$ | 4-methylpiperazin-1-yl N-oxide |
| 272 | saturated | H | H | >C(H)(OH)- | H | $OCOCH_3$ | 2-pyridyl | imidazol-1-yl |
| 273 | saturated | H | H | >C(H)(OH)- | H | $OCOC_2H_5$ | $CCl_3$ | pyrazol-1-yl |
| 274 | saturated | H | H | >C(H)(OH)- | H | $OCOC_3H_7$ | H | $-N(CH_3)(C_2H_5) \to O$ |

-continued

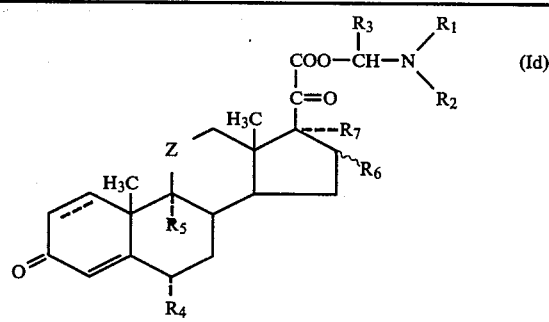

| Example Number | Δ¹ | R₄ | R₅ | Z | R₆ | R₇ | R₃ | —N(R₁)(R₂) |
|---|---|---|---|---|---|---|---|---|
| 275 | saturated | H | H | >C(H)(OH) | H | —OC(=O)C₆H₅ | H | indol-1-yl |
| 276 | unsaturated | H | F | >C(H)(OH) | β-CH₃ | OH | H | imidazol-1-yl |
| 277 | unsaturated | H | F | >C(H)(OH) | β-CH₃ | OH | CCl₃ | pyrazol-1-yl |
| 278 | unsaturated | H | F | >C(H)(OH) | β-CH₃ | OH | C₆H₅C(=O)— | —N(→O)(CH₃)₂ |
| 279 | unsaturated | H | F | >C(H)(OH) | β-CH₃ | OCOC₄H₉ | H | 2,4,6-trimethylanilino (N(CH₃)) |
| 280 | unsaturated | H | F | >C(H)(OH) | β-CH₃ | —OC(=O)C₆H₅ | H | imidazol-1-yl |
| 281 | unsaturated | H | F | >C(H)(OH) | α-CH₃ | OH | 4-pyridyl | —N(→O)(CH₃)₂ |
| 282 | unsaturated | H | F | >C(H)(OH) | α-CH₃ | OH | H | pyrazol-1-yl |

-continued

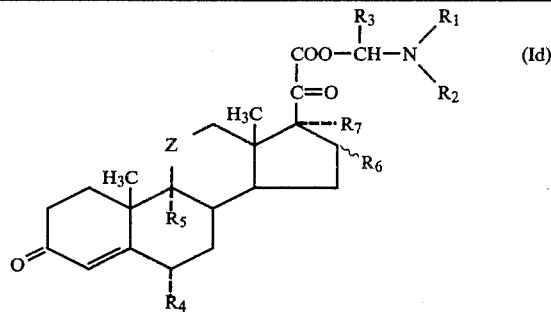

| Example Number | Δ¹ | R₄ | R₅ | Z | R₆ | R₇ | R₃ | $-N\begin{matrix}R_1\\R_2\end{matrix}$ |
|---|---|---|---|---|---|---|---|---|
| 283 | unsaturated | H | F | >C(H)(OH) | α-CH₃ | OH | CCl₃ | -N(imidazolyl) |
| 284 | unsaturated | H | F | >C(H)(OH) | α-CH₃ | -OC(=O)C₆H₅ | H | -N(2,4,6-trimethylphenyl)(CH₃) |
| 285 | unsaturated | H | F | >C(H)(OH) | α-CH₃ | OCOCH₃ | CCl₃ | -N(→O)(CH₃)(C₂H₅) |
| 286 | unsaturated | H | F | >C(H)(OH) | H | OH | H | -N(pyrazolyl) |
| 287 | unsaturated | H | H | >C(H)(OH) | H | OH | CCl₃ | -N(imidazolyl) |
| 288 | unsaturated | H | H | >C(H)(OH) | H | OH | -C(=O)C₆H₅ | -N(→O)(C₂H₅)(C₂H₅) |
| 289 | unsaturated | H | H | >C(H)(OH) | H | -OC(=O)C₆H₅ | H | -N(2,4,6-trimethylphenyl)(CH₃) |
| 290 | unsaturated | H | H | >C(H)(OH) | H | OCOC₃H₇ | H | -N(→O)-piperazinyl-N-CH₃ |
| 291 | unsaturated | H | F | >C(H)(OH) | α-OH | OH | -C(=O)C₆H₅ | -N(imidazolyl) |

-continued

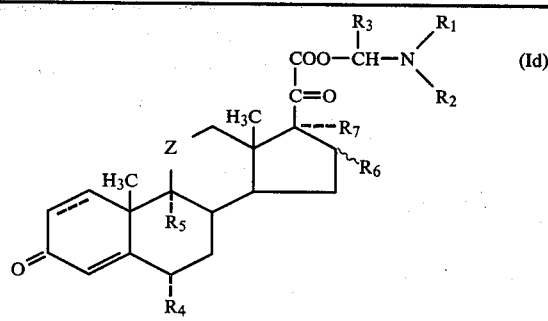

(Id)

| Example Number | Δ¹ | R₄ | R₅ | Z | R₆ | R₇ | R₃ | —N(R₁)(R₂) |
|---|---|---|---|---|---|---|---|---|
| 292 | unsaturated | H | F | >C(H)(OH) | α-OH | OH | 4-pyridyl | N(O)(CH₃)(C₂H₅) |
| 293 | unsaturated | H | F | >C(H)(OH) | α-OH | OH | H | N(CH₃)(2,4,6-trimethylphenyl) |
| 294 | unsaturated | H | F | >C(H)(OH)—O—C(CH₃)₂—O— (acetonide) | α-O— | —O— | H | pyrazol-1-yl |
| 295 | unsaturated | H | F | >C(H)(OH)—O—C(CH₃)₂—O— (acetonide) | α-O— | —O— | CCl₃ | imidazol-1-yl |
| 296 | unsaturated | H | F | >C(H)(OH) | α-OCOCH₃ | OCOCH₃ | —C(O)CH₃ | morpholine N-oxide |
| 297 | unsaturated | H | F | >C(H)(OH)—O—C(CH₃)₂—O— (acetonide) | α-O— | —O— | H | N(O)(CH₃)₂ |
| 298 | unsaturated | F | H | >C(H)(OH) | α-CH₃ | H | H | pyrazol-1-yl |
| 299 | unsaturated | F | H | >C(H)(OH) | α-CH₃ | H | CCl₃ | imidazol-1-yl |
| 300 | unsaturated | F | H | >C(H)(OH) | α-CH₃ | H | —C(O)CH₃ | N(O)(CH₃)₂ |

-continued

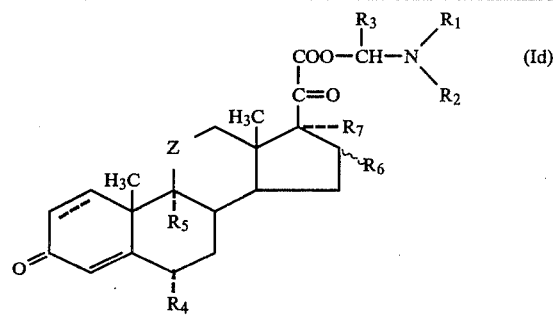
(Id)

| Example Number | Δ¹ | R₄ | R₅ | Z | R₆ | R₇ | R₃ | —N(R₁)(R₂) |
|---|---|---|---|---|---|---|---|---|
| 301 | unsaturated | F | H | >CH(OH) | α-CH₃ | H | —C(=O)—C₆H₅ | imidazol-1-yl |
| 302 | unsaturated | F | H | >CH(OH) | α-CH₃ | H | 4-pyridyl | N(CH₃)(2,4,6-trimethylphenyl) |
| 303 | unsaturated | F | H | >CH(OH) | α-CH₃ | H | H | 4-methylpiperazin-1-yl |
| 304 | saturated | H | H | >C=O | H | OH | H | pyrazol-1-yl |
| 305 | saturated | H | F | >CH(OH) | H | OH | H | pyrazol-1-yl |
| 306 | unsaturated | Cl | H | >C=O | H | OH | H | pyrazol-1-yl |
| 307 | unsaturated | F | F | >CH(OH) | α-CH₃ | OH | H | imidazol-1-yl |
| 308 | unsaturated | F | H | >CH(OH) | H | OH | H | imidazol-1-yl |
| 309 | unsaturated | H | H | >C=O | β-CH₃ | OH | H | pyrazol-1-yl |

-continued

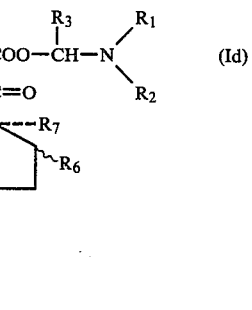
(Id)

| Example Number | Δ¹ | $R_4$ | $R_5$ | Z | $R_6$ | $R_7$ | $R_3$ | $-N\begin{matrix}R_1\\R_2\end{matrix}$ |
|---|---|---|---|---|---|---|---|---|
| 310 | unsaturated | $CH_3$ | H | >C(H)(OH)- | H | OH | H | -N-pyrazolyl |
| 311 | unsaturated | F | H | >C(H)(OH)- | α-$CH_3$ | OH | H | -N-pyrazolyl |
| 312 | unsaturated | H | H | >C=O | H | OH | H | -N-pyrazolyl |
| 313 | saturated | F | H | >C(H)(OH)--O--C($CH_3$)($CH_3$)-- (acetonide) | | H | H | -N-pyrazolyl |
| 314 | unsaturated | H | F | >C(H)(OH)--O--C($C_2H_5$)($C_2H_5$)-- | | H | H | -N-pyrazolyl |
| 315 | unsaturated | H | F | >C(H)(OH)--O--C($CH_3$)(phenyl)-- | | H | H | -N-pyrazolyl |
| 316 | unsaturated | F | Cl | >C(H)(OH)- | α-$CH_3$ | H | H | -N($CH_3$)($CH_3$)→O |
| 317 | unsaturated | H | H | >C(H)(OH)--O--C($CH_3$)($CH_3$)-- | | H | H | -N-pyrazolyl |
| 318 | unsaturated | H | F | >C(H)(OH)- | α-$CH_3$ | H | $CCl_3$ | -N-pyrazolyl |

-continued

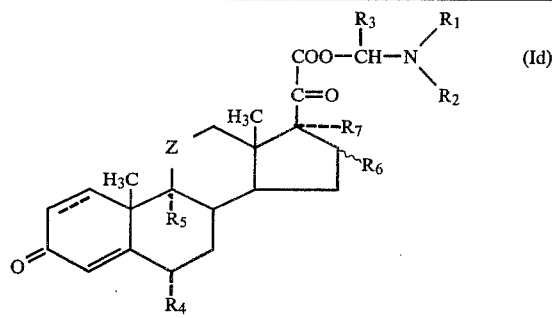

| Example Number | Δ¹ | $R_4$ | $R_5$ | Z | $R_6$ | $R_7$ | $R_3$ | $-N\begin{smallmatrix}R_1\\R_2\end{smallmatrix}$ |
|---|---|---|---|---|---|---|---|---|
| 319 | unsaturated | F | F | >C(H)(OH) | H | $OCOC_3H_7$ | H | pyrazol-1-yl |
| 320 | unsaturated | F | H | >C(H)(OH)—O—C($CH_3$)($CH_3$)—O— (acetonide) | | O—C($CH_3$)($CH_3$)—O— | $CCl_3$ | imidazol-1-yl |
| 321 | unsaturated | F | F | >C(H)(OH)—O—C($CH_3$)($CH_3$)—O— (acetonide) | | O—C($CH_3$)($CH_3$)—O— | H | $-N(C_2H_5)_2 \rightarrow O$ |
| 322 | saturated | H | H | >C=O | H | OH | $CCl_3$ | imidazol-1-yl |
| 323 | saturated | H | F | >C(H)(OH) | H | $OCOC_6H_5$ | H | pyrazol-1-yl |
| 324 | unsaturated | Cl | H | >C=O | H | $OCOC_3H_7$ | H | pyrazol-1-yl |
| 325 | unsaturated | F | F | >C(H)(OH) | α-$CH_3$ | $OCOC_2H_5$ | H | pyrrol-1-yl |
| 326 | unsaturated | F | H | >C(H)(OH) | H | $OCOCH_3$ | H | 2,4,6-trimethylanilino |
| 327 | unsaturated | H | H | >C=O | β-$CH_3$ | $OCOC_3H_7$ | H | imidazol-1-yl |

-continued

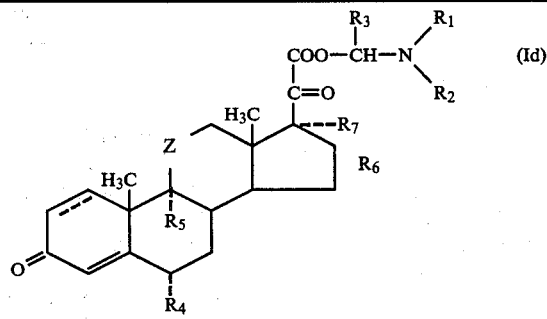

| Example Number | Δ¹ | R₄ | R₅ | Z | R₆ | R₇ | R₃ | $-N\begin{smallmatrix}R_1\\R_2\end{smallmatrix}$ |
|---|---|---|---|---|---|---|---|---|
| 328 | unsaturated | CH₃ | H | >C(H)(OH) | H | OCO—Ph | H | $-N(C(O)CH_3)(CH_3)$ (see structure) |
| 329 | unsaturated | F | H | >C(H)(OH) | α-CH₃ | OCOCH₃ | H | pyrrolyl |
| 330 | unsaturated | H | H | >C(H)(OH) | H | OCO—Ph | H | pyrrolyl |

From the foregoing description, one of ordinary skill in the art can easily ascertain the essential characteristics of the instant invention, and without departing from the spirit and scope thereof, can make various changes and/or modifications of the instant invention to adapt it to various usages and conditions. As such, these changes and/or modifications are properly, equitably and intended to be, within the full range of the equivalence of the following claims.

What is claimed is:

1. A compound selected from the group consisting of:
(a) compounds having the structural formula:

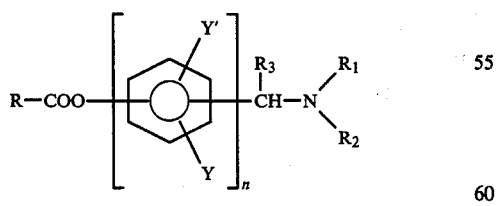

wherein R—COO— is the acyloxy residue of the cephalosporin antibiotic containing one carboxylic acid function; Y and Y', which can be the same or different, and each hydrogen or alkyl of 1 to 4 carbon atoms; n is zero or one; the depicted phenylene group is oriented such that R—COO— and

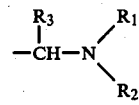

are positioned ortho or para to each other; $R_1$ and $R_2$, which can be the same or different, are each alkyl or 1 to 10 carbon atoms; alkenyl of 2 to 10 carbon atoms; aryl of 6 to 10 carbon atoms; cycloalkyl or 3 to 8 carbon atoms; cycloalkenyl of 4 to 8 carbon atoms; alkynyl or 2 to 10 carbon atoms; aralkyl, alkaryl, aralkenyl, aralkynyl, alkenylaryl, or alkynylaryl, wherein the alkyl, alkenyl, alkynyl, and aryl portions are defined as above; or a substituted derivative of one of the above-defined alkyl, alkenyl, aryl, cycloalkyl, cycloalkenyl, alkynyl, aralkyl, alkaryl, aralkenyl, aralkynyl, alkenylaryl and alkynylaryl radicals, said derivative having one or more substituents each of which are selected from the group consisting of $C_1$-$C_8$alkyl, $C_1$-$C_8$alkoxy, $C_1$-$C_8$alkanoyl, $C_1$-$C_8$alkanoyloxy, halo, cyano, $C_2$-$C_9$carbalkoxy, $C_1$-$C_8$alkylthio, nitro, $C_1$-$C_8$haloalkyl having 1 or more halo substituents, dialkylamino wherein the alkyl portions each contain 1 to 8 carbon atoms, carboxy, dialkylcarbamyl wherein the alkyl portions each contain 1 to 8 carbon atoms, and $C_1$-$C_8$alkylsulfonyl; or $R_1$ and $R_2$ are combined so that —$NR_1R_2$ represents the residue of a saturated or unsaturated heterocyclic compound containing one secondary nitrogen atom; and $R_3$ is hydrogen, $R_{1'}$,

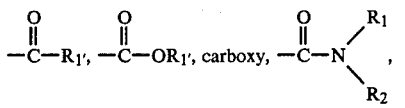

—CH$_2$OCOR$_{1'}$, —CH$_2$ONO$_2$, CX$_3$, 2-pyridyl, 3-pyridyl, 4-pyridyl, 2-furyl, cyano, carbamyl or C$_2$–C$_9$alkylcarbamyl, wherein R$_1$ and R$_2$ are as defined above, X is Cl or Br and R$_{1'}$ is any radical encompassed by the definition of R$_1$ above; and (b) the non-toxic pharmaceutically acceptable acid addition salts and N-oxides thereof.

2. A compound as defined by claim 1, wherein R—COO— is the acyloxy residue of a compound selected from the group consisting of cefmetazole, cefazolin, cephalexin, cefoxitin, cephacetrile, cephalogylcin, cephaloridine, cephalothin, cephapirin and cephradine.

3. A compound as defined by claim 2, wherein R—COO— is the acyloxy residue of cefmetazole.

4. A compound as defined by claim 2, wherein R—COO— is the acyloxy residue of cefazolin.

5. A compound as defined by claim 2, wherein R—COO— is the acyloxy residue of cephalexin.

6. A compound as defined by claim 1, wherein R—COO— is the acyloxy residue of a penicillin antibiotic containing one carboxylic acid function.

7. A compound as defined by claim 6, wherein R—COO— is the acyloxy residue of a compound selected from the group consisting of ampicillin, amoxicillin, hetacillin, carfecillin, carindacillin, amylpenicillin, azidocillin, benzylpenicillinic acid, clometacillin, cloxacillin, cyclacillin, methicillin, nafcillin, 2-pentenylpenicillin, penicillin BT, penicillin O, penicillin S, penicillin V, chlorobutin penicillin, dicloxacillin, diphenicillin, heptylpenicillin and metampicillin.

8. A compound as defined by claim 7, wherein R—COO— is the acyloxy residue of ampicillin.

9. A compound as defined by claim 7, wherein R—COO— is the acyloxy residue of penicillin V.

10. A compound as defined by claim 7, wherein R—COO— is the acyloxy residue of amoxicillin.

11. A compound as defined by claim 7, wherein R—COO— is the acyloxy residue of hetacillin.

12. A compound selected from the group consisting of:
(a) compounds having the structural formula:

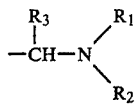

are positioned ortho or para to each other; R$_1$ and R$_2$, which can be the same or different, are each alkyl or 1 to 10 carbon atoms; alkenyl of 2 to 10 carbon atoms; aryl of 6 to 10 carbon atoms; cycloalkyl or 3 to 8 carbon atoms; cycloalkenyl of 4 to 8 carbon atoms; alkynyl or 2 to 10 carbon atoms; aralkyl, alkaryl, aralkenyl, aralkynyl, alkenylaryl, or alkynylaryl, wherein the alkyl, alkenyl, alkynyl, and aryl portions are defined as above; or a substituted derivative of one of the above-defined alkyl, alkenyl, aryl, cycloalkyl, cycloalkenyl, alkynyl, aralkyl, alkaryl, aralkenyl, aralkynyl, alkenylaryl and alkynylaryl radicals, said derivative having one or more substituents each of which are selected from the group consisting of C$_1$–C$_8$alkyl, C$_1$–C$_8$alkoxy, C$_1$–C$_8$alkanoyl, C$_1$–C$_8$alkanoyloxy, halo, cyano, C$_2$–C$_9$carbalkoxy, C$_1$–C$_8$alkylthio, nitro, C$_1$–C$_8$haloalkyl having 1 or more halo substituents, dialkylamino wherein the alkyl portions each contain 1 to 8 carbon atoms, carboxy, dialkylcarbamyl wherein the alkyl portions each contain 1 to 8 carbon atoms, and C$_1$–C$_8$alkylsulfonyl; or R$_1$ and R$_2$ are combined so that —NR$_1$R$_2$ represents the residue of a saturated or unsaturated heterocyclic compound containing one secondary nitrogen atom; and R$_3$ is hydrogen, R$_{1'}$,

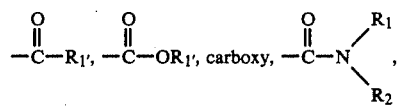

—CH$_2$OCOR$_{1'}$, —CH$_2$ONO$_2$, CX$_3$, 2-pyridyl, 3-pyridyl, 4-pyridyl, 2-furyl, cyano, carbamyl or C$_2$–C$_9$alkylcarbamyl, wherein R$_1$ and R$_2$ are as defined above, X is Cl or Br and R$_{1'}$ is any radical encompassed by the definition of R$_1$ above; and (b) the non-toxic pharmaceutically acceptable acid addition salts and N-oxides thereof.

13. A compound as defined by claim 12, wherein —OOC—R'—COO— is the di(acyloxy) residue of

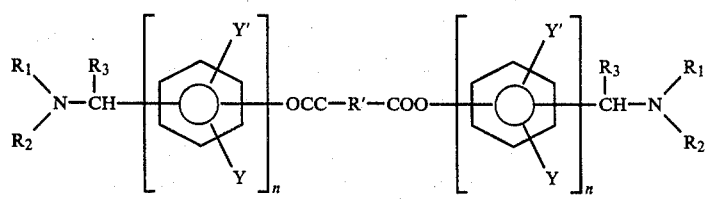

wherein —OOC—R'—COO— is the di(acyloxy) residue of a bio-affecting dicarboxylic acid selected from the group consisting of methotrexate, carbenicillin, penicillin N, and glutathione; Y and Y', which can be the same or different, and each hydrogen or alkyl of 1 to 4 carbon atoms; n is zero or one; the depicted phenylene group is oriented such that R—COO— and methotrexate.

14. A compound as defined by claim 12, wherein —OOC—R'—COO— is the di(acyloxy) residue or glutathione.

15. A pharmaceutical composition of matter comprising an antibiotic effective amount of a compound selected from the group consisting of:
(a) compounds having the structural formula:

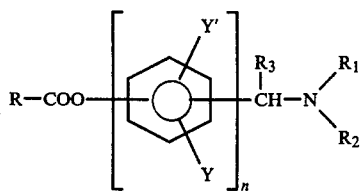

wherein R—COO— is the acyloxy residue of a cephalosporin antibiotic containing one carboxylic acid function; Y and Y', which can be the same or different, and each hydrogen or alkyl of 1 to 4 carbon atoms; n is zero or one; the depicted phenylene group is oriented such that R—COO— and

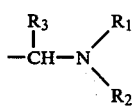

are positioned ortho or para to each other; $R_1$ and $R_2$, which can be the same or different, are each alkyl or 1 to 10 carbon atoms; alkenyl of 2 to 10 carbon atoms; aryl of 6 to 10 carbon atoms; cycloalkyl or 3 to 8 carbon atoms; cycloalkenyl of 4 to 8 carbon atoms; alkynyl or 2 to 10 carbon atoms; aralkyl, alkaryl, aralkenyl, aralkynyl, alkenylaryl, or alkynylaryl, wherein the alkyl, alkenyl, alkynyl, and aryl portions are defined as above; or a substituted derivative of one of the above-defined alkyl, alkenyl, aryl, cycloalkyl, cycloalkenyl, alkynyl, aralkyl, alkaryl, aralkenyl, aralkynyl, alkenylaryl and alkynylaryl radicals, said derivative having one or more substituents each of which are selected from the group consisting of $C_1$–$C_8$alkyl, $C_1$–$C_8$alkoxy, $C_1$–$C_8$alkanoyl, $C_1$–$C_8$alkanoyloxy, halo, cyano, $C_2$–$C_9$carbalkoxy, $C_1$–$C_8$-alkylthio, nitro, $C_1$–$C_8$haloalkyl having 1 or more halo substitutents, dialkylamino wherein the alkyl portions each contain 1 to 8 carbon atoms, carboxy, dialkylcarbamyl wherein the alkyl portions each contain 1 to 8 carbon atoms, and $C_1$–$C_8$alkylsulfonyl; or $R_1$ and $R_2$ are combined so that —$NR_1R_2$ represents the residue of a saturated or unsaturated heterocyclic compound containing one secondary nitrogen atom; and $R_3$ is hydrogen, $R_{1'}$,

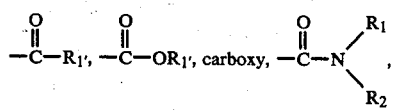

—$CH_2OCOR_{1'}$, —$CH_2ONO_2$, $CX_3$, 2-pyridyl, 3-pyridyl, 4-pyridyl, 2-furyl, cyano, carbamyl or $C_2$–$C_9$alkylcarbamyl, wherein $R_1$ and $R_2$ are as defined above, X is Cl or Br and $R_1$ and $R_2$, which can be the same or different, are each alkyl or 1 to 10 carbon atoms; alkenyl of 2 to 10 carbon atoms; aryl of 6 to 10 carbon atoms; cycloalkyl or 3 to 8 carbon atoms; cycloalkenyl of 4 to 8 carbon atoms; alkynyl or 2 to 10 carbon atoms; aralkyl, alkaryl, aralkenyl, aralkynyl, alkenylaryl, or alkynylaryl, wherein the alkyl, alkenyl, alkynyl, and aryl portions are defined as above; or a substituted derivative of one of the above-defined alkyl, alkenyl, aryl, cycloalkyl, cycloalkenyl, alkynyl, aralkyl, alkaryl, aralkenyl, aralkynyl, alkenylaryl and alkynylaryl radicals, said derivative having one or more substituents each of which are selected from the group consisting of $C_1$–$C_8$alkyl, $C_1$–$C_8$alkoxy, $C_1$–$C_8$alkanoyl, $C_1$–$C_8$alkanoyloxy, halo, cyano, $C_2$–$C_9$carbalkoxy, $C_1$–$C_8$alkylthio, nitro, $C_1$–$C_8$haloalkyl having 1 or more halo substituents, dialkylamino wherein the alkyl portions each contain 1 to 8 carbon atoms, carboxy, dialkylcarbamyl wherein the alkyl portions each contain 1 to 8 carbon atoms, and $C_1$–$C_8$alkylsulfonyl; or $R_1$ and $R_2$ are combined so that —$NR_1R_2$ represents the residue of a saturated or unsaturated heterocyclic compound containing one secondary nitrogen atom; and $R_3$ is hydrogen, $R_{1'}$,

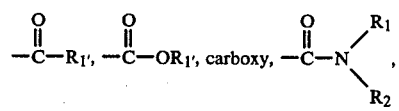

—$CH_2OCOR_{1'}$, —$CH_2ONO_2$, $CX_3$, 2-pyridyl, 3-pyridyl, 4-pyridyl, 2-furyl, cyano, carbamyl or $C_2$–$C_9$alkylcarbamyl, wherein $R_1$ and $R_2$ are as defined above, X is Cl or Br $R_{1'}$ is any radical encompassed by the definition of $R_1$ above; and (b) the non-toxic pharmaceutically acceptable acid addition salts and N-oxides thereof, and a pharmaceutically acceptable carrier therefor.

16. A method of eliciting an antibiotic response in a warm-blooded animal, which comprises administering to such animal an antibiotic effective amount of a compound selected from the group consisting of:

(a) compounds having the structural formula:

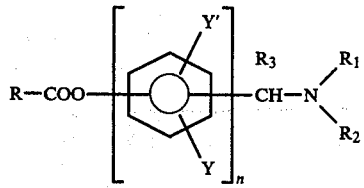

wherein R—COO— is the acyloxy residue of a cephalosporin antibiotic containing one carboxylic acid function; Y and Y', which can be the same or different, and each hydrogen or alkyl of 1 to 4 carbon atoms; n is zero or one; the depicted phenylene group is oriented such at R—COO— and

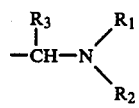

are positioned ortho or para to each other; and $R_{1'}$ is any radical encompassed by the definition of $R_1$ above; and (b) the non-toxic pharmaceutically accetable acid addition salts and N-oxides thereof.

17. A pharmaceutical composition of matter comprising an antibiotic effective amount of a compound selected from the group consisting of:

(a) compounds having the structural formula:

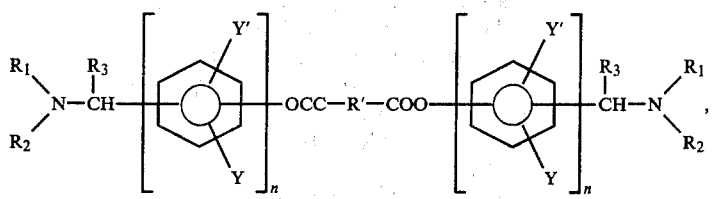

wherein —OOC—R'—COO— is the di(acyloxy) residue of a bio-affecting dicarboxylic acid selected from the group consisting of methotrexate, carbenicillin, penicillin n, and glutathione; Y and Y', which can be the same or different, and each hydrogen or alkyl of 1 to 4 carbon atoms; n is zero or one; the depicted phenylene group is oriented such that R—COO— and

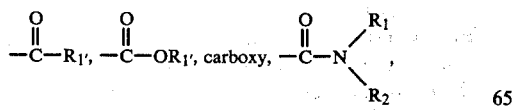

are positioned ortho or para to each other; $R_1$ and $R_2$, which can be the same or different, are each alkyl or 1 to 10 carbon atoms; alkenyl of 2 to 10 carbon atoms; aryl of 6 to 10 carbon atoms; cycloalkyl or 3 to 8 carbon atoms; cycloalkenyl of 4 to 8 carbon atoms; alkynyl or 2 to 10 carbon atoms; aralkyl, alkaryl, aralkenyl, aralkynyl, alkenylaryl, or alkynylaryl, wherein the alkyl, alkenyl, alkynyl, and aryl portions are defined as above; or a substituted derivative of one of the above-defined alkyl, alkenyl, aryl, cycloalkyl, cycloalkenyl, alkynyl, aralkyl, alkaryl, aralkenyl, aralkynyl, alkenylaryl and alkynylaryl radicals, said derivative having one or more substituents each of which are selected from the group consisting of $C_1$-$C_8$alkyl, $C_1$-$C_8$alkoxy, $C_1$-$C_8$alkanoyl, $C_1$-$C_8$alkanoyloxy, halo, cyano, $C_2$-$C_9$carbalkoxy, $C_1$-$C_8$alkylthio, nitro, $C_1$-$C_8$haloalkyl having 1 or more halo substituents, dialkylamino wherein the alkyl portions each contain 1 to 8 carbon atoms, carboxy, dialkylcarbamyl wherein the alkyl portions each contain 1 to 8 carbon atoms, and $C_1$-$C_8$alkylsulfonyl; or $R_1$ and $R_2$ are combined so that —$NR_1R_2$ represents the residue of a saturated or unsaturated heterocyclic compound containing one secondary nitrogen atom; and $R_3$ is hydrogen, $R_{1'}$, $$-\overset{O}{\overset{\|}{C}}-R_{1'}, \quad -\overset{O}{\overset{\|}{C}}-OR_{1'}, \text{ carboxy, } -\overset{O}{\overset{\|}{C}}-N\overset{R_1}{\underset{R_2}{\diagdown}},$$

—$CH_2OCOR_{1'}$, —$CH_2ONO_2$, $CX_3$, 2-pyridyl, 3-pyridyl, 4-pyridyl, 2-furyl, cyano, carbamyl or $C_2$-$C_9$alkylcarbamyl, wherein $R_1$ and $R_2$ are as defined above, X is Cl or Br and $R_1$, is any radical encompassed by the definition of $R_1$ above; and (b) the non-toxic pharmaceutically acceptable acid addition salts and N-oxides thereof, and a pharmaceutically acceptable carrier therefor.

18. A method of eliciting an antibiotic response in a warm-blooded animal, which comprises administering to such animal an antibiotic effective amount of a compound selected from the group consisting of:

(a) compounds having the structural formula:

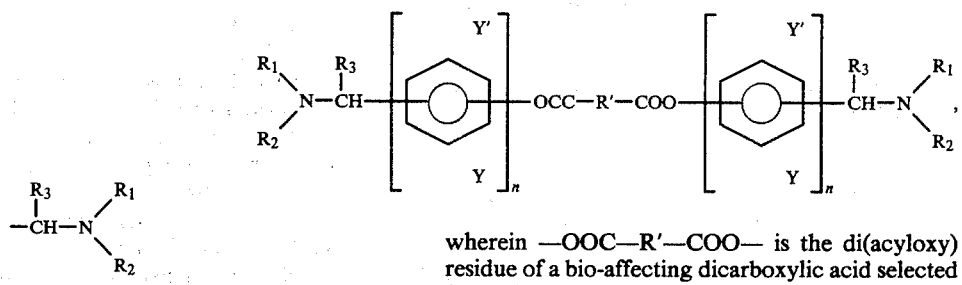

wherein —OOC—R'—COO— is the di(acyloxy) residue of a bio-affecting dicarboxylic acid selected from the group consisting of methotrexate, carbenicillin, penicillin N, and glutathione; Y and Y', which can be the same or different, and each hydrogen or alkyl of 1 to 4 carbon atoms; n is zero or one; the depicted phenylene group is oriented such that R—COO— and

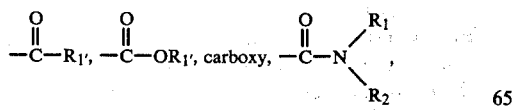

are positioned ortho or para to each other; $R_1$ and $R_2$, which can be the same or different, are each alkyl or 1 to 10 carbon atoms; alkenyl of 2 to 10 carbon atoms; aryl of 6 to 10 carbon atoms; cycloalkyl or 3 to 8 carbon atoms; cycloalkenyl of 4 to 8 carbon atoms; alkynyl or 2 to 10 carbon atoms; aralkyl, alkaryl, aralkenyl, aralkynyl, alkenylaryl, or alkynylaryl, wherein the alkyl, alkenyl, alkynyl, and aryl portions are defined as above; or a substituted derivative of one of the above-defined alkyl, alkenyl, aryl, cycloalkyl, cycloalkenyl, alkynyl, aralkyl, alkaryl, aralkenyl, aralkynyl, alkenylaryl and alkynylaryl radicals, said derivative having one or more substituents each of which are selected from the group consisting of $C_1$-$C_8$alkyl, $C_1$-$C_8$alkoxy, $C_1$-$C_8$alkanoyl, $C_1$-$C_8$alkanoyloxy, halo, cyano, $C_2$-$C_9$carbalkoxy, $C_1$-$C_8$alkylthio, nitro, $C_1$-$C_8$haloalkyl having 1 or more halo substituents, dialkylamino wherein the alkyl portions each contain 1 to 8 carbon atoms, carboxy, dialkylcarbamyl wherein the alkyl portions each contain 1 to 8 carbon atoms, and $C_1$-$C_8$alkylsulfonyl; or $R_1$ and $R_2$ are combined so that —$NR_1R_2$ represents the residue of a saturated or unsaturated heterocyclic compound containing one secondary nitrogen atom; and $R_3$ is hydrogen, $R_{1'}$,

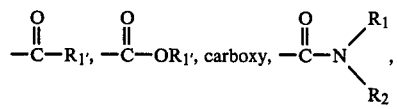

—$CH_2OCOR_{1'}$, —$CH_2ONO_2$, $CX_3$, 2-pyridyl, 3-pyridyl, 4-pyridyl, 2-furyl, cyano, carbamyl or $C_2$-$C_9$alkylcarbamyl, wherein $R_1$ and $R_2$ are as defined above, X is Cl or Br and $R_{1'}$ is any radical encompassed by the definition of $R_1$ above; and (b) the non-toxic pharmaceutically acceptable acid addition salts and N-oxides thereof.

19. A compound as defined by claim 1 or 12, wherein R—COO— is the acyloxy residue of a cephalosporin antibiotic containing one carboxylic acid function or of a penicillin antibiotic containing one carboxylic acid function.

20. A compound as defined by claim 19, wherein R—COO— is the acyloxy residue of a compound selected from the group consisting of cefmetazole, cefazolin, cefalexin, cefoxitin, cephacetrile, cephaloglycin, cephaloridine, cephalothin, cephapirin, cephradine, ampicillin, amoxicillin, hetacillin, carfecillin, carindacillin, amylpenicillin, azidocillin, benzylpenicillinic acid, clometacillin, cloxacillin, cyclacillin, methicillin, nafcillin, 2-pentenylpenicillin, penicillin BT, penicillin O, penicillin S, penicillin V, chlorobutin penicillin, dicloxacillin, diphenicillin, heptylpenicillin and metampicillin.

21. A compound as defined by claim 20, wherein R—COO— is the acyloxy residue of a compound selected from the group consisting of cephalexin, cefmetazole, cefazolin, cefoxitin, ampicillin, hetacillin, amoxicillin and amylpenicillin.

22. A compound as defined by claim 2, wherein R—COO— is the acyloxy residue of cefoxitin.

23. A compound as defined by claim 7, wherein R—COO— is the acyloxy residue of amylpenicillin.

24. The compound as defined by claim 21, wherein R—COO— is the acyloxy residue of cephalexin, n is zero, $R_3$ is hydrogen and —$NR_1R_2$ is 1-imidazolyl.

25. The compound as defined by claim 21, wherein R—COO— is the acyloxy residue of cefmetazole, n is zero, $R_3$ is $CCl_3$ and —$NR_1R_2$ is 1-imidazolyl.

26. The compound as defined by claim 21, wherein R—COO— is the acyloxy residue of cefazolin, n is zero, $R_3$ is

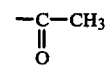

and —$NR_1R_2$ is 1-imidazolyl.

27. The compound as defined by claim 21, wherein R—COO— is the acyloxy residue of cefoxitin, n is zero, $R_3$ is hydrogen and —$NR_1R_2$ is 1-imidazolyl.

28. The compound as defined by claim 21, wherein R—COO— is the acyloxy residue of ampicillin, n is zero, $R_3$ is $CCl_3$ and —$NR_1R_2$ is 1-imidazolyl.

29. The compound as defined by claim 21, wherein R—COO— is the acyloxy residue of hetacillin, n is zero, $R_3$ is $CCl_3$ and —$NR_1R_2$ is 1-imidazolyl.

30. The compound as defined by claim 21, wherein R—COO— is the acyloxy residue of amoxicillin, n is zero, $R_3$ is

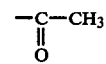

and —$NR_1R_2$ is 1-imidazolyl.

31. The compound as defined by claim 21, wherein R—COO— is the acyloxy residue of amylpenicillin, n is zero, $R_3$ is hydrogen and —$NR_1R_2$ is 1-imidazolyl.

* * * * *